US009540622B2

(12) United States Patent
Sukumaran et al.

(10) Patent No.: US 9,540,622 B2
(45) Date of Patent: Jan. 10, 2017

(54) ENGINEERED BIOCATALYSTS USEFUL FOR CARBAPENEM SYNTHESIS

(71) Applicant: Codexis, Inc., Redwood City, CA (US)

(72) Inventors: Joly Sukumaran, Singapore (SG); Derek Smith, Singapore (SG); Hong Yang, Singapore (SG); Wan Lin Yeo, Singapore (SG); Jeffrey C. Moore, Westfield, NJ (US)

(73) Assignee: Codexis, Inc., Redwood City, CA (US)

( * ) Notice: Subject to any disclaimer, the term of this patent is extended or adjusted under 35 U.S.C. 154(b) by 44 days.

(21) Appl. No.: 14/760,963

(22) PCT Filed: Jan. 16, 2014

(86) PCT No.: PCT/US2014/011767

§ 371 (c)(1),
(2) Date: Jul. 14, 2015

(87) PCT Pub. No.: WO2014/113521

PCT Pub. Date: Jul. 24, 2014

(65) Prior Publication Data

US 2015/0353976 A1 Dec. 10, 2015

Related U.S. Application Data

(60) Provisional application No. 61/754,095, filed on Jan. 18, 2013.

(51) Int. Cl.

| | |
|---|---|
| ***C12N 9/18*** | (2006.01) |
| ***C12P 11/00*** | (2006.01) |
| ***C12P 17/18*** | (2006.01) |

(52) U.S. Cl.

CPC .................. *C12N 9/18* (2013.01); *C12P 11/00* (2013.01); *C12P 17/184* (2013.01); *C12Y 301/01* (2013.01); *Y02P 20/52* (2015.11)

(58) Field of Classification Search

None

See application file for complete search history.

(56) References Cited

U.S. PATENT DOCUMENTS

| | | | |
|---|---|---|---|
| 4,194,047 | A | 3/1980 | Christensen et al. |
| 4,292,436 | A | 9/1981 | Liu et al. |
| 4,374,772 | A | 2/1983 | Hazen et al. |
| 4,894,450 | A | 1/1990 | Grabowski et al. |
| 5,245,069 | A | 9/1993 | McManus |
| 5,468,632 | A | 11/1995 | Cantwell et al. |
| 5,741,691 | A | 4/1998 | Arnold et al. |
| 5,906,930 | A | 5/1999 | Arnold et al. |
| 5,945,325 | A | 8/1999 | Arnold et al. |
| 6,117,679 | A | 9/2000 | Stemmer |
| 6,376,246 | B1 | 4/2002 | Crameri et al. |
| 6,537,746 | B2 | 3/2003 | Arnold et al. |
| 6,586,182 | B1 | 7/2003 | Patten et al. |
| 7,462,712 | B2 | 12/2008 | Kumar et al. |
| 7,647,184 | B2 | 1/2010 | Vega et al. |
| 9,029,107 | B2 | 5/2015 | Kawabata et al. |
| 9,061,991 | B2 * | 6/2015 | Asuma .................... C07B 53/00 |
| 2002/0095034 | A1 | 7/2002 | Zenoni et al. |
| 2006/0195947 | A1 | 8/2006 | Davis et al. |
| 2006/0257890 | A1 | 11/2006 | Minshull et al. |
| 2008/0220990 | A1 | 9/2008 | Fox |
| 2009/0258406 | A1 | 10/2009 | Michels et al. |
| 2009/0312196 | A1 | 12/2009 | Colbeck et al. |

FOREIGN PATENT DOCUMENTS

| | | | |
|---|---|---|---|
| EP | 0551750 | A2 | 7/1993 |
| WO | 95/22625 | A1 | 8/1995 |
| WO | 95/33836 | A1 | 12/1995 |
| WO | 96/00787 | A1 | 1/1996 |
| WO | 97/0078 | A1 | 1/1997 |
| WO | 97/35966 | A1 | 10/1997 |
| WO | 98/27230 | A1 | 6/1998 |
| WO | 00/42651 | A1 | 7/2000 |
| WO | 01/75767 | A2 | 10/2001 |
| WO | 2009/008908 | A2 | 1/2009 |
| WO | 2012/029819 | A1 | 3/2012 |
| WO | 2014/113521 | A1 | 7/2014 |

OTHER PUBLICATIONS

Wierdl et al. (Biochemistry 2004, 43, 1874-1882).*

Song et al. ("Genome Sequence of the Plant Growth-Promoting *Rhizobacterium bacillus* sp. Strain JS" J. Bacteriol. 194:3760-3761(2012).*

Wada, K., et al., "Codon usage tabulated from the GenBank genetic sequence data," Nucl. Acids Res., 20:2111-2118 [1992].

Wells, J.A., et al., "Cassette mutagenesis: an efficient method for generation of multiple mutations at defined sites," Gene, 34:315-323 (1985).

Wetmur, J. G., "DNA Probes: Applications of the Principles of Nucleic Acid Hybridization," Crit Rev Biochem Mol Biol, 26(3/4):227-259 (1991).

Wright, F., "The 'effective number of codons' used in a gene," Gene 87:23-29 [1990].

Yi, S., et al., "Covalent immobilization of omega-transaminase from Vibrio fluvialis JS17 on chitosan beads," Process Biochemistry 42(5): 895-898 (2007).

Zhang, J-H., et al., "Directed evolution of a fucosidase from a galactosidase by DNA shuffling and screening ,"Proc. Nat. Acad. Sci., U.S.A., 94:4504-4509 (1997).

(Continued)

*Primary Examiner* — Suzanne M Noakes

*Assistant Examiner* — Jae W Lee

(74) *Attorney, Agent, or Firm* — Codexis, Inc.

(57) ABSTRACT

The present disclosure provides engineered pNB esterase polypeptides useful for the synthesis of the carbapenem antibiotic, imipenem. The disclosure also provides polynucleotides encoding the engineered pNB esterases, host cells capable of expressing the engineered pNB esterases, and methods of using the engineered pNB esterases in the production of imipenem.

32 Claims, No Drawings

(56) References Cited

OTHER PUBLICATIONS

Zhao, H., et al., "Molecular evolution by staggered extension process (StEP) in vitro recombination," Nat. Biotechnol., 16:258-261 (1998).
Zock, J., et al., "The Bacillus subtilis pnbA gene encoding p-nitrobenzyl esterase: cloning, sequence and high-level expression in *Escherichia coli*," Gene,151(1-2): 37-43 (1994).
Genbank Accession No. AAA81915.1 dated Nov. 21, 2011.
Altschul, S., et al., "Basic local alignment search tool," J. Mol. Biol., 215: 403-410 (1990).
Altschul, S.F., et al., "Gapped BLAST and PSI-BLAST: a new generation of protein database search programs," Nucleic Acids Res., 25(17):3389-3402 (1997).
Baldino, Jr., F., et al., "High-Resolution in Situ Hybridization Histochemistry," Methods Enzymology, 168:761-777 (1989).
Batzer, M.A., "Erratum: Structure and variability of recently inserted Alu family members", Nucleic Acids Res 19:698-699 [1991].
Beaucage, S.L., et al., "Deoxynucleoside phosphoamidites—A new class of key intermediates for deoxypolynucleotide synthesis," Tetrahedron Letters, 22(20):1859-62 (1981).
Black, M.E., et al., "Creation of drug-specific herpes simplex virus type 1 thymidine kinase mutants for gene therapy," Proc Natl Acad Sci USA, 93:3525-3529 (1996).
Bolton, E.T., et al., "A General Method for the Iisolation of RNA Complementary to DNA," Proc. Natl. Acad. Sci. USA 48:1390 (1962).
Botstein, D., et al., "Strategies and applications of in vitro mutagenesis," Science, 229(4719):1193-1201 [1985].
Bray, P., et al., "Human cDNA clones for four species of G., signal transduction protein," Proc. Natl. Acad. Sci USA, 83:8893-8897 [1986].
Caldwell, R.C., et al., "Mutagenic PCR," PCR Methods Appl., 3:S136-S140 (1994).
Carter, P., "Site-directed mutagenesis," Biochem. J., 237:1-7 (1986).
Christians, F.C., et al., "Directed evolution of thymidine kinase for AZT phosphorylation using DNA family shuffling," Nat. Biotechnol., 17:259-264 (1999).
Crameri, A., et al., "DNA shuffling of a family of genes from diverse species accelerates directed evolution", Nature, 391:288-291 (1998).
Crameri, A., et al., "Improved green fluorescent protein by molecular evolution using DNA shuffling," Nat. Biotechnol., 14(3):315-319 (1996).
Crameri, A., et al., "Molecular evolution of an arsenate detoxification pathway by DNA shuffling," Nat. Biotechnol., 15(5):436-438 (1997).
Dale, S.J., et al., "Oligonucleotide-directed random mutagenesis using the phosphorothioate method," Methods Mol. Biol., 57:369-74 (1996).
De Boer, H.A., et al., "The tac promoter: A functional hybrid derived from the trp and lac promoters," Proc. Natl Acad. Sci. USA, 80: 21-25 (1983).
Fasman, G.D.,CRC Practical Handbook of Biochemistry and Molecular Biology, CRC Press, Boca Raton, FL, pp. 3-70 [1989].
Freier, S.M., et al., "Improved free-energy parameters for predictions of RNA duplex stability," Proc. Natl. Acad. Sci USA, 83:9373-9377 (1986).
Giver, L., et al., "Directed evolution of a thermostable esterase," Proc. Natl. Acad. Sci. USA, 95: 12809-12813 [1998].
Guo, Z., et al., "3'-End-Forming Signals of Yeast mRNA," Mol. Cell. Biol., 15(11):5983-5990 [1995].
Henaut and Danchin in Neidhardt et al. [eds.], *Escherichia coli* and *Salmonella*, "Analysis and predictions from *Escherichia coli* Sequences, or *E. coli* in silico," ASM Press, Washington D.C., [1987], pp. 2047-2066.
Henikoff, S.,et al., "Amino acid substitution matrices from protein blocks," Proc. Natl. Acad. Sci., 89:10915-10919 (1992).
Kierzek, R., et al., "Polymer-Supported RNA Synthesis and Its Application to Test the Nearest-Neighbor Model for Duplex Stability," Biochemistry, 25:7840-7846 (1986).
Koszelewski, D., et al., "Immobilization of omega-transaminases by encapsulation in a sol-gel/celite matrix," Journal of Molecular Catalysis B: Enzymatic, 63: 39-44 (2010).
Kramer, B., et al., "Different base/base mismatches are corrected with different efficiencies by the methyl-directed DNA mismatch-repair system of *E. coli*," Cell, 38(3):879-887, 1984.
Ling, M., et al., "Approaches to DNA Mutagenesis:An Overview," Anal. Biochem., 254:157-78 (1997).
Martin, A.R., et al., "Characterization of free and immobilized (S)-aminotransferase for acetophenone production," Applied Microbiology and Biotechnology, 76(4): 843-851 (2007).
Mateo, C., et al., "Epoxy sepabeads: a novel epoxy support for stabilization of industrial enzymes via very intense multipoint covalent attachment," Biotechnology Progress 18(3):629-34 (2002).
Matthes, H.W.D., et al., "Simultaneous rapid chemical synthesis of over one hundred oligonucleotides on a microscale," EMBO J., 3(4):801-05 (1984).
McInerney, J.O., "GCUA: general codon usage analysis," Bioinformatics, 14(4):372-73 [1998].
Minshull, J., et al., "Protein evolution by molecular breeding," Curr. Op. Chem. Biol., 3(3):284-290 (1999).
Moore, J.C., et al. "Strategies for the in vitro Evolution of Protein Function: Enzyme Evolution by Random Recombination of Improved Sequences," J. Mol. Biol., 272(3):336-347 (1997).
Moore, J.C., et al., "Directed evolution of a para-nitrobenzyl esterase for aqueous-organic solvents," Nature Biotechnology, 14: 458-467 (1996).
Nakamura, Y., et al., "Codon usage tabulated from international DNA sequence databases: status for the year 2000," Nucl. Acids Res., 28:292 [2000].
Needleman, S., et al., "A general method applicable to the search for similarities in the amino acid sequence of two proteins," J. Mol. Biol. 48:443-453 (1970).
Pearson, W.R., "Improved tools for biological sequence comparison," Proc. Nat'l. Acad. Sci. USA, 85:2444-2448 (1988).
Romanos, M.A., et al., "Foreign gene expression in yeast: a review," Yeast 8:423-488 [1992].
Rychlik, W., et al., "Optimization of the annealing temperature for DNA amplification in vitro," Nucleic Acids Res, 18(21):6409-6412 (1990).
Simonen, M., et al., "Protein Secretion in *Bacillus* Species," Microbiological Reviews, 57:109-137 (1993).
Smith, M., "In vitro mutagenesis," Ann. Rev. Genet., 19:423-462 (1985).
Smith, T., et al., "Comparison of Biosequences," Adv. Appl. Math, 2:482-489 (1981).
Stemmer, W., "DNA Shuffling by Random Fragmentation and Reassembly: In vitro Recombination for Molecular Evolution," Proc. Natl. Acad. Sci. USA, 91:10747-10751 (1994).
Stemmer, W.P.C., "Rapid evolution of a protein in vitro by DNA shuffling", Nature, 370:389-391 (1994).
Stenico, M., et al., "Codon usage in Caenorhabditis elegans: delineation of translational selection and mutational biases," Nucl. Acids Res. 22(13):2437-46 [1994].
Suggs, S.V., et al., "Use of synthetic oligodeoxyribonucleotides for the isolation of specific cloned DNA sequenes," In Developmental Biology Using Purified Genes (Brown et al., eds.), pp. 683-693, Academic Press (1981).
Tiwari, S., et al., "Prediction of probable genes by Fourier analysis of genomic sequences," Comput. Appl. Biosci. 13(3):263-270 [1997].
Truppo, M.D., et al., "Development of an Improved Immobilized CAL-B for the Enzymatic Resolution of a Key Intermediate to Odanacatib," Organic Process Research & Development, 15:1033-1035 (2011).
Uberbacher, E.C., et al., "Discovering and Understanding Genes in Human DNA Sequence Using GRAIL," Methods Enzymol., 266:259-281 [1996].
Villa-Komaroff, L., et al., "A bacterial clone synthesizing proinsulin," Proc. Natl Acad. Sci. USA, 75:3727-3731 (1978).

(56) References Cited

OTHER PUBLICATIONS

Database WPI Week 201224, Accession No. 2012-D03226 dated Mar. 8, 2012.

* cited by examiner

SEQUENCE LISTING

<160> NUMBER OF SEQ ID NOS: 120

<210> SEQ ID NO 1
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 1

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gttttacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcatga gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                         1467
```

<210> SEQ ID NO 2
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 2

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
```

-continued

```
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460
```

```
Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 3
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 3

atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gttttacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgcga gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                         1467


<210> SEQ ID NO 4
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 4

Met Thr His Gln Ile Val Thr Thr Gln Tyr Gly Lys Val Lys Gly Thr
1               5                   10                  15
```

```
Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Ala Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430
```

```
Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 5
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 5

atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gtattacctg ggtgccggta gcgagtcgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgcga gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                        1467


<210> SEQ ID NO 6
<211> LENGTH: 489
<212> TYPE: PRT
<213> ORGANISM: Artificial Sequence
<220> FEATURE:
<223> OTHER INFORMATION: Engineered variant of B. subtilis pNB esterase
```

<400> SEQUENCE: 6

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Glu Ser Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Ala Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
```

-continued

```
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 7
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 7

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gtattacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgcga gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

<210> SEQ ID NO 8

```
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 8

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Ala Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380
```

```
Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 9
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 9

atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gttttacctg ggtgccggta gctggccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgcga gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc  tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440
```

```
cagaagctgt tcccgagcaa gggtgaa                                     1467


<210> SEQ ID NO 10
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 10

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Trp Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Ala Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350
```

```
Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 11
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 11

atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gttttacctg ggtgccggta gccagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgcga gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260
```

```
atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467


<210> SEQ ID NO 12
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 12

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Gln Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Ala Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
```

```
            325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
            405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
            485
```

<210> SEQ ID NO 13
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 13

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gttttacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgtta gcattgccgc gctgctggcc    600

atgccggctg cgaaaggcct gtttcaaaag gcgattatgg ggagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac     960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140
```

```
tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                      1467
```

```
<210> SEQ ID NO 14
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 14

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Gly Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300
```

```
Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 15
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 15

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gttttacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgcga gcattgccgc gctgctggcc    600

atgccggctg cgaaaggcct gtttcaaaag gcgattatgg agagcggtgc aagcgatacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960
```

```
gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

```
<210> SEQ ID NO 16
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 16

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Ala Ser Ile Ala Ala Leu Leu Ala Met Pro Ala Ala Lys Gly Leu Phe
        195                 200                 205

Gln Lys Ala Ile Met Glu Ser Gly Ala Ser Asp Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270
```

```
Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 17
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 17

atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gttttacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgcga gcattgccgc gctgctggcc    600

atgccggctg cgaaaggcct gtttcaaaag gcgattatgg agagcggtgc aagcctgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttccagcc tgcactggat    840
```

```
ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467


<210> SEQ ID NO 18
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 18

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Ala Ser Ile Ala Ala Leu Leu Ala Met Pro Ala Ala Lys Gly Leu Phe
        195                 200                 205

Gln Lys Ala Ile Met Glu Ser Gly Ala Ser Leu Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
```

```
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

```
<210> SEQ ID NO 19
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 19

atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300

gtttggattc acggcggtgc gttttacctg ggtgccggta gcgagccgct gtacgatggc     360

tccaagctgg ctgcgcaagg tgaggtcatt gtcgtcaccc tgaactatcg tctgggcccg     420

ttcggtttca tgcacctgag cagcttcgat gaggcgtata gcgacaattt gggtctgctg     480

gaccaagcgg cagccctgaa atgggttcgc gagaacatca gcgcgtttgg tggcgacccg     540

gataatgtga cggtgtttgg tgaaagcgct ggtggcgcga gcattgccgc gctgctggcc     600

atgccggctg cgaaaggcct gtttcaaaag gcgattatgg agagcggtgc aagccgtacc     660
```

```
atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggagt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

```
<210> SEQ ID NO 20
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 20

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Ala Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220
```

```
Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Glu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

```
<210> SEQ ID NO 21
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 21

atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300

gtttggattc acggcggtgc gttttacctg ggtgccggta gcgagccgct gtacgatggc     360

tccaagctgg ctgcgcaagg tgaggtcatt gtcgtcaccc tgaactatcg tctgggcccg     420

ttcggtttca tgcacctgag cagcttcgat gaggcgtata gcgacaattt gggtctgctg     480

gaccaagcgg cagccctgaa atgggttcgc gagaacatca gcgcgtttgg tggcgacccg     540
```

```
gataatgtga cggtgtttgg tgaaagcgct ggtggcgcga gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttccatcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467


<210> SEQ ID NO 22
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 22

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190
```

```
Ala Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe His Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 23
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 23

```
atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300

gtttggattc acggcggtgc gttttacctg ggtgccggta gcgagccgct gtacgatggc     360
```

-continued

```
tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgcga gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttcactcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467


<210> SEQ ID NO 24
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 24

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
```

```
                165                 170                 175

Gly Gly Asp Pro Asp Asn Val Thr Val Phe Gly Glu Ser Ala Gly Gly
            180                 185                 190

Ala Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Thr Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 25
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 25

atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240
```

```
gattgtctgt acgttaatgt ttttgcgccg gataccccgt cccaaaatct gccggttatg    300

gtttggattc acggcggtgc gttttacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgcga gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttcctgcc tgcactggat    840

ccgaaaactt tgccggaaga gccggaaaaa tccattgcgg aaggtgcggc aagcggtatt    900

ccgctgttga ttggcaccac gcgcgacgaa ggttacctgt tttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttaccatga agaaacccgt   1380

gaaaccgtga tcctggactc tgagattacc atcgagaatg accctgagag cgagaagcgt   1440

cagaagctgt tcccgagcaa gggtgaa                                        1467
```

```
<210> SEQ ID NO 26
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 26

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140
```

```
His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Ala Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Leu Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 27
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 27

```
atgacccatc aaatcgtcac cactcagtac ggcaaagtca aaggtacgac ggagaacggt     60
```

```
gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt tttgcgccg gataccccgt cccaaaatct gccggttatg    300

gtttggattc acggcggtgc gttttacctg ggtgccggta gcgagccgct gtacgatggc    360

tccaagctgg ctgcgcaagg tgaggtcact gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgcga gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttccatcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467


<210> SEQ ID NO 28
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 28

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110
```

```
Gly Ser Glu Pro Leu Tyr Asp Gly Ser Lys Leu Ala Ala Gln Gly Glu
        115                 120                 125

Val Thr Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Ala Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe His Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 29
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 29

```
atgacccatc aaatcgtcac cactcagtac ggcaaagtca aaggtacgac ggagaacggt     60
gttcataagt ggaaaggcat cccgtatgcg aagccgccag tgggccagtg gcgtttcaaa    120
gcgccggaac cgccggaggt ctgggaggat gttctggacg caaccgcgta tggtcctgtc    180
tgcccacagc cgtcggacct gttgagcctg agctatacgg aactgccacg tcagagcgaa    240
gattgtctgt acgttaatgt ttttgcgccg gataccccgt cccaaaatct gccggttatg    300
gtttggattc acggcggtgc gttttacctg ggtgccggta gcgagccgct gtacgatggc    360
tccaagctgg ctgcgcaagg tgaggtcatt gtcgtcaccc tgaactatcg tctgggcccg    420
ttcggtttca tgcacctgag cagcttcgat gaggcgtata gcgacaattt gggtctgctg    480
gaccaagcgg cagccctgaa atgggttcgc gagaacatca gcgcgtttgg tggcgacccg    540
gataatgtga cggtgtttgg tgaaagcgct ggtggcgcga gcattgccgc gctgctggcc    600
atgccggctg cgaaaggcct gtttcaaaag gcgattatgg agagcggtgc aagccgtacc    660
atgaccaagg aacaagcggc gagcactgcg gcagcttttc tgcaagtgct gggtatcaat    720
gagagccagc tggatcgttt gcacaccgtc gcagcggagg acctgctgaa ggcagctgac    780
caactgcgta tcgcggagaa agagaatatc ttccagctgt tcttccagcc tgcactggat    840
ccgaaaactt tgccggaaga gccggaaaaa tccattgcgg aaggtgcggc aagcggtatt    900
ccgctgttga ttggtaccac gcgcgacgaa ggttacctgt ttttcacgtc tgatagcgac    960
gttcgtagcc aggaaacctt ggacgctgcg ctggagtaca gcctgggcaa gccgttggca   1020
gagaaagcgg cggacttgta cccgcgcagc ctggaatccc aaatccacat ggtgaccgat   1080
ctggattttt ggcgcccagc cgtggcattc gcgtctgcac agagccatta cgcaccggtg   1140
tggatgtatc gcttcgattg gcacccggag aaaccgccgt acaacaaagc cttccacgcc   1200
ctggagctgc cgtttgtttt cggtaacctg gatggcttgg aacgtatggc caaagccgaa   1260
atcacggacg aggttaagca actgtcccac acgattcaga gcgcctggat tacgtttgca   1320
aagaccggca acccgagcac cgaggcggtg aactggccgg cttatcatga agaaacccgt   1380
gaaaccgtga tcctggactc tgagattacc atcgagaatg accctgagag cgagaagcgt   1440
cagaagctgt tcccgagcaa gggtgaa                                       1467
```

<210> SEQ ID NO 30
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 30

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
```

```
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Ala Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Asp Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485

<210> SEQ ID NO 31
```

<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 31

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gttttacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgcga gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac     960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgtcttttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

<210> SEQ ID NO 32
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 32

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60
```

```
Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Ala Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Ser Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480
```

```
Gln Lys Leu Phe Pro Ser Lys Gly Glu
                485


<210> SEQ ID NO 33
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 33

atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300

gtttggattc acggcggtgc gttttacctg ggtgccggta gcgagccgct gtacgatggc     360

tccaagctgg ctgcgcaagg tgaggtcatt gtcgtcaccc tgaactatcg tctgggcccg     420

ttcggtttca tgcacctgag cagcttcgat gaggcgtata gcgacaattt gggtctgctg     480

gaccaagcgg cagccctgaa atgggttcgc gagaacatca gcgcgtttgg tggcgacccg     540

gataatgtga cggtgtttgg tgaaagcgct ggtggcgcga gcattgccgc gctgctggcc     600

atgccggctg cgaaaggcct gtttcaaaag gcgattatgg agagcggtgc aagccgtacc     660

atgaccaagg aacaagcggc gagcactgcg gcagcttttc tgcaagtgct gggtatcaat     720

gagagccagc tggatcgttt gcacaccgtc gcagcggagg acctgctgaa ggcagctgac     780

caactgcgta tcgcggagaa agagaatatc ttccagctgt tcttccagcc tgcactggat     840

ccgaaaactt tgccggaaga gccggaaaaa tccattgcgg aaggtgcggc aagcggtatt     900

ccgctgttga ttggtaccac gcgcgacgaa ggttacctgt tttcacgtc tgatagcgac     960

gttcgtagcc aggaaacctt ggacgctgcg ctggagtaca gcctgggcaa gccgttggca    1020

gagaaagcgg cggacttgta cccgcgcagc ctggaatccc aaatccacat ggtgaccgat    1080

ctgcagtttt ggcgcccagc cgtggcattc gcgtctgcac agagccatta cgcaccggtg    1140

tggatgtatc gcttcgattg gcacccggag aaaccgccgt acaacaaagc cttccacgcc    1200

ctggagctgc cgtttgtttt cggtaacctg gatggcttgg aacgtatggc caaagccgaa    1260

atcacggacg aggttaagca actgtcccac acgattcaga gcgcctggat tacgtttgca    1320

aagaccggca acccgagcac cgaggcggtg aactggccgg cttatcatga agaaacccgt    1380

gaaaccgtga tcctggactc tgagattacc atcgagaatg accctgagag cgagaagcgt    1440

cagaagctgt tcccgagcaa gggtgaa                                        1467


<210> SEQ ID NO 34
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 34

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30
```

```
Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Ala Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Gln Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
```

450 455 460

Leu Asp Ser Glu Ile Thr Ile Glu Asn Asp Pro Glu Ser Glu Lys Arg
465 470 475 480

Gln Lys Leu Phe Pro Ser Lys Gly Glu
485

<210> SEQ ID NO 35
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 35

```
atgacccatc aaatcgtcac cactcagtac ggcaaagtca aaggtacgac ggagaacggt     60
gttcataagt ggaaaggcat cccgtatgcg aagccgccag tgggccagtg gcgtttcaaa    120
gcgccggaac cgccggaggt ctgggaggat gttctggacg caaccgcgta tggtcctgtc    180
tgcccacagc cgtcggacct gttgagcctg agctatacgg aactgccacg tcagagcgaa    240
gattgtctgt acgttaatgt ttttgcgccg gataccccgt cccaaaatct gccggttatg    300
gtttggattc acggcggtgc gttttacctg ggtgccggta gcgagccgct gtacgatggc    360
tccaagctgg ctgcgcaagg tgaggtcatt gtcgtcaccc tgaactatcg tctgggcccg    420
ttcggtttca tgcacctgag cagcttcgat gaggcgtata gcgacaattt gggtctgctg    480
gaccaagcgg cagccctgaa atgggttcgc gagaacatca gcgcgtttgg tggcgacccg    540
gataatgtga cggtgtttgg tgaaagcgct ggtggcgaga gcattgccgc gctgctggcc    600
atgccggctg cgaaaggcct gtttcaaaag gcgattatgg agagcggtgc aagccgtacc    660
atgaccaagg aacaagcggc gagcactgcg gcagcttttc tgcaagtgct gggtatcaat    720
gagagccagc tggatcgttt gcacaccgtc gcagcggagg acctgctgaa ggcagctgac    780
caactgcgta tcgcggagaa agagaatatc ttccagctgt tcttccagcc tgcactggat    840
ccgaaaactt tgccggaaga gccggaaaaa tccattgcgg aaggtgcggc aagcggtatt    900
ccgctgttga ttggtaccac gcgcgacgaa ggttacctgt tttcacgtc tgatagcgac     960
gttcgtagcc aggaaacctt ggacgctgcg ctggagtaca gcctgggcaa gccgttggca   1020
gagaaagcgg cggacttgta cccgcgcagc ctggaatccc aaatccacat ggtgaccgat   1080
ctgctgtttt ggcgcccagc cgtggcattc gcgtctgcac agagccatta cgcaccggtg   1140
tggatgtatc gcttcgattg gcacccggag aaaccgccgt acaacaaagc cttccacgcc   1200
ctggagctgc cgtttgtttt cggtaacctg gatggcttgg aacgtatggc caaagccgaa   1260
atcacggacg aggttaagca actgtcccac acgattcaga gcgcctggat tacgtttgca   1320
aagaccggca acccgagcac cgaggcggtg aactggccgg cttatcatga agaaacccgt   1380
gaaaccgtga tcctggactc tgagattacc atcgagaatg accctgagag cgagaagcgt   1440
cagaagctgt tcccgagcaa gggtgaa                                       1467
```

<210> SEQ ID NO 36
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 36

Met Thr His Gln Ile Val Thr Thr Gln Tyr Gly Lys Val Lys Gly Thr

```
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Glu Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430
```

```
Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 37
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 37

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt tttgcgccg gataccccgt cccaaaatct gccggttatg    300

gtttggattc acggcggtgc gttttacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgata gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

<210> SEQ ID NO 38
<211> LENGTH: 489
<212> TYPE: PRT
<213> ORGANISM: Artificial Sequence
<220> FEATURE:

<223> OTHER INFORMATION: Engineered variant of B. subtilis pNB esterase

<400> SEQUENCE: 38

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Asp Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400
```

```
Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 39
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 39

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gctgtacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgtca gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac     960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                        1467
```

```
<210> SEQ ID NO 40
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 40

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Leu Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
```

```
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 41
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 41

atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gttttacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgtca gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggttt tcttcgcgcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac     960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380
```

```
gaaaccgtga tcctggactc tgagattacc atcgagaatg accctgagag cgagaagcgt   1440

cagaagctgt tcccgagcaa gggtgaa                                       1467


<210> SEQ ID NO 42
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 42

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Val Phe Phe Ala Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350
```

```
Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 43
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 43

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gttttacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgtca gcattgccgc gctgctggcc    600

atgccggctg cgaaaggcct gtttcaaaag gcgattatgg agagcggtgc aagcgtgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggttt tcttcgcgcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctggtgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260
```

```
atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467


<210> SEQ ID NO 44
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 44

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Val Phe Phe Ala Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320
```

```
Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Val Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 45
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 45

```
atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300

gtttggattc acggcggtgc gctttacctg ggtgccggta gcgagccgct gtacgatggc     360

tccaagctgg ctgcgcaagg tgaggtcatt gtcgtcaccc tgaactatcg tctgggcccg     420

ttcggtttca tgcacctgag cagcttcgat gaggcgtata gcgacaattt gggtctgctg     480

gaccaagcgg cagccctgaa atgggttcgc gagaacatca gcgcgtttgg tggcgacccg     540

gataatgtga cggtgtttgg tgaaagcgct ggtggcgcca gcattgccgc gctgctggcc     600

atgccggctg cgaaaggcct gtttcaaaag gcgattatgg agagcggtgc aagcgtgacc     660

atgaccaagg aacaagcggc gagcactgcg gcagcttttc tgcaagtgct gggtatcaat     720

gagagccagc tggatcgttt gcacaccgtc gcggcggagg acctgctgaa ggcagctgac     780

caactgcgta tcgcggagaa agagaatatc ttccaggttt tcttccagcc tgcactggat     840

ccgaaaactt tgccggaaga gccggaaaaa tccattgcgg aaggtgcggc aagcggtatt     900

ccgctgttga ttggtaccac gcgcgacgaa ggttacctgt ttttcacgtc tgatagcgac     960

gttcgtagcc aggaaacctt ggacgctgcg ctggagtaca gcctgggcaa gccgttggca    1020

gagaaagcgg cggacttgta cccgcgcagc ctggaatccc aaatccacat ggtgaccgat    1080
```

```
ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                      1467


<210> SEQ ID NO 46
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 46

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Leu Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Ala Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Val Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
```

```
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 47
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 47

atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300

gtttggattc acggcggtgc gctgtacctg ggtgccggta gcgagccgct gtacgatggc     360

tccaagctgg ctgcgcaagg tgaggtcatt gtcgtcaccc tgaactatcg tctgggcccg     420

ttcggtttca tgcacctgag cagcttcgat gaggcgtata gcgacaattt gggtctgctg     480

gaccaagcgg cagccctgaa atgggttcgc gagaacatca gcgcgtttgg tggcgacccg     540

gataatgtga cggtgtttgg tgaaagcgct ggtggcatga gcattgccgc gctgctggcc     600

atgccggctg cgaaaggcct gtttcaaaag gcgattatgg agagcggtgc aagcgtgacc     660

atgaccaagg aacaagcggc gagcactgcg gcagcttttc tgcaagtgct gggtatcaat     720

gagagccagc tggaccgttt gcacaccgtc gcagcggagg acctgctgaa ggcagctgac     780

caactgcgta tcgcggagaa agagaatatc ttccaggttt tcttccagcc tgcactggat     840

ccgaaaactt tgccggaaga gccggaaaaa tccattgcgg aaggtgcggc aagcggtatt     900

ccgctgttga ttggtaccac gcgcgacgaa ggttacctgt tttcacgtc tgatagcgac      960
```

```
gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                      1467
```

```
<210> SEQ ID NO 48
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 48

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Leu Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270
```

```
Val Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 49
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 49

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gttttacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgtca gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780
```

```
caactgcgta tcgcggagaa agagaatatc ttccaggttt tcttcgcgcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac     960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctggcgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                         1467
```

<210> SEQ ID NO 50
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 50

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240
```

```
Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Val Phe Phe Ala Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Ala Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 51
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 51

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gttttacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgtca gcattgccgc gctgctggcc    600

atgccggctg cgaaaggcct gtttcaaaag gcgattatgg agagcggtgc aagcgcgacc    660
```

```
atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggttt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctggtgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                        1467
```

```
<210> SEQ ID NO 52
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 52

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Ala Thr Met Thr Lys Glu
```

```
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Val Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Val Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 53
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 53

atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300

gtttggattc acggcggtgc gttttacctg ggtgccggta gcgagccgct gtacgatggc     360

tccaagctgg ctgcgcaagg tgaggtcatt gtcgtcaccc tgaactatcg tctgggcccg     420

ttcggtttca tgcacctgag cagcttcgat gaggcgtata gcgacaattt gggtctgctg     480
```

```
gaccaagcgg cagccctgaa atgggttcgc gagaacatca gcgcgtttgg tggcgacccg    540

gataatgtga cggtgtttgg tgaaagcgct ggtggcgtca gcattgccgc gctgctggcc    600

atgccggctg cgaaaggcct gtttcaaaag gcgattatgg agagcggtgc aagcgtgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggctt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                        1467
```

```
<210> SEQ ID NO 54
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 54

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190
```

```
Val Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

```
<210> SEQ ID NO 55
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 55

atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300

gtttggattc acggcggtgc gttttacctg ggtgccggta gcgagccgct gtacgatggc     360
```

```
tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgtca gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggctt tcttcgcgcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac    960

gctcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctggcgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                        1467
```

```
<210> SEQ ID NO 56
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 56

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160
```

```
Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Ala Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Ala Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Ala Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

```
<210> SEQ ID NO 57
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 57

atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180
```

```
tgcccacagc cgtcggacct gttgagcctg agctatacgg aactgccacg tcagagcgaa    240
gattgtctgt acgttaatgt ttttgcgccg gataccccgt cccaaaatct gccggttatg    300
gtttggattc acggcggtgc gttttacctg ggtgccggta gcgagccgct gtacgatggc    360
tccaagctgg ctgcgcaagg tgaggtcatt gtcgtcaccc tgaactatcg tctgggcccg    420
ttcggtttca tgcacctgag cagcttcgat gaggcgtata gcgacaattt gggtctgctg    480
gaccaagcgg cagccctgaa atgggttcgc gagaacatca gcgcgtttgg tggcgacccg    540
gataatgtga cggtgtttgg tgaaagcgct ggtggcgtca gcattgccgc gctgctggcc    600
atgccggctg cgaaaggcct gtttcaaaag gcgattatgg agagcggtgc aagcgcgacc    660
atgaccaagg aacaagcggc gagcactgcg gcagcttttc tgcaagtgct gggtatcaat    720
gagagccagc tggatcgttt gcacaccgtc gcagcggagg acctgctgaa ggcagctgac    780
caactgcgta tcgcggagaa agagaatatc ttccaggctt tcttcgcgcc tgcactggat    840
ccgaaaactt tgccggaaga gccggaaaaa tccattgcgg aaggtgcggc aagcggtatt    900
ccgctgttga ttggtaccac gcgcgacgaa ggttacctgt tttcacgtc tgatagcgac    960
gttcgtagcc aggaaacctt ggacgctgcg ctggagtaca gcctgggcaa gccgttggca   1020
gagaaagcgg cggacttgta cccgcgcagc ctggaatccc aaatccacat ggtgaccgat   1080
ctggtgtttt ggcgcccagc cgtggcattc gcgtctgcac agagccatta cgcaccggtg   1140
tggatgtatc gcttcgattg gcacccggag aaaccgccgt acaacaaagc cttccacgcc   1200
ctggagctgc cgtttgtttt cggtaacctg gatggcttgg aacgtatggc caaagccgaa   1260
atcacggacg aggttaagca actgtcccac acgattcaga gcgcctggat tacgtttgca   1320
aagaccggca acccgagcac cgaggcggtg aactggccgg cttatcatga agaaacccgt   1380
gaaaccgtga tcctggactc tgagattacc atcgagaatg accctgagag cgagaagcgt   1440
cagaagctgt tcccgagcaa gggtgaa                                       1467
```

```
<210> SEQ ID NO 58
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 58

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
```

-continued

```
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Ala Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Ala Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Val Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 59
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 59

atgacccatc aaatcgtcac cactcagtac ggcaaagtca aaggtacgac ggagaacggt      60
```

```
gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gctgtacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcatga gcattgccgc gctgctggcc    600

atgccggctg cgaaaggcct gtttcaaaag gcgattatgg agagcggtgc aagcgtgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagttat tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctggcgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

```
<210> SEQ ID NO 60
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 60

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Leu Tyr Leu Gly Ala
            100                 105                 110
```

```
Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Ala Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 61
<211> LENGTH: 1467
<212> TYPE: DNA
<213> ORGANISM: Artificial Sequence
<220> FEATURE:

<223> OTHER INFORMATION: Engineered variant of B. subtilis pNB esterase

<400> SEQUENCE: 61

```
atgacccatc aaatcgtcac cactcagtac ggcaaagtca aaggtacgac ggagaacggt     60
gttcataagt ggaaaggcat cccgtatgcg aagccgccag tgggccagtg gcgtttcaaa    120
gcgccggaac cgccggaggt ctgggaggat gttctggacg caaccgcgta tggtcctgtc    180
tgcccacagc cgtcggacct gttgagcctg agctatacgg aactgccacg tcagagcgaa    240
gattgtctgt acgttaatgt ttttgcgccg gataccccgt cccaaaatct gccggttatg    300
gtttggattc acggcggtgc gctgtacctg ggtgccggta gcgagccgct gtacgatggc    360
tccaagctgg ctgcgcaagg tgaggtcatt gtcgtcaccc tgaactatcg tctgggcccg    420
ttcggtttca tgcacctgag cagcttcgat gaggcgtata gcgacaattt gggtctgctg    480
gaccaagcgg cagccctgaa atgggttcgc gagaacatca gcgcgtttgg tggcgacccg    540
gataatgtga cggtgtttgg tgaaagcgct ggtggcatga gcattgccgc gctgctggcc    600
atgccggctg cgaaaggcct gtttcaaaag gcgattatgg agagcggtgc aagcgtgacc    660
atgaccaagg aacaagcggc gagcactgcg gcagcttttc tgcaagtgct gggtatcaat    720
gagagccagc tggatcgttt gcacaccgtc gcagcggagg acctgctgaa ggcagctgac    780
caactgcgta tcgcggagaa agagaatatc ttccagttat tcttccagcc tgcactggat    840
ccgaaaactt tgccggaaga gccggaaaaa tccattgcgg aaggtgcggc aagcggtatt    900
ccgctgttga ttggtaccac gcgcgacgaa ggttacctgt tttcacgtc tgatagcgac    960
gttcgtagcc aggaaacctt ggacgctgcg ctggagtaca gcctgggcaa gccgttggca   1020
gagaaagcgg cggacttgta cccgcgcagc ctggaatccc aaatccacat ggtgaccgat   1080
ctggtgtttt ggcgcccagc cgtggcattc gcgtctgcac agagccatta cgcaccggtg   1140
tggatgtatc gcttcgattg gcacccggag aaaccgccgt acaacaaagc cttccacgcc   1200
ctggagctgc cgtttgtttt cggtaacctg gatggcttgg aacgtatggc caaagccgaa   1260
atcacggacg aggttaagca actgtcccac acgattcaga gcgcctggat tacgtttgca   1320
aagaccggca acccgagcac cgaggcggtg aactggccgg cttatcatga agaaacccgt   1380
gaaaccgtga tcctggactc tgagattacc atcgagaatg accctgagag cgagaagcgt   1440
cagaagctgt tcccgagcaa gggtgaa                                       1467
```

<210> SEQ ID NO 62
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 62

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80
```

```
Asp Cys Leu Tyr Val Asn Val Phe Ala Pro Asp Thr Pro Ser Gln Asn
                85                  90                  95

Leu Pro Val Met Val Trp Ile His Gly Gly Ala Leu Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Val Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 63
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 63

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gctgtacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgtca gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggctt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctggcgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

<210> SEQ ID NO 64
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 64

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
```

```
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Leu Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Ala Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480
```

```
Gln Lys Leu Phe Pro Ser Lys Gly Glu
                485

<210> SEQ ID NO 65
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 65

atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gttttacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgtca gcattgccgc gctgctggcc    600

atgccggctg cgaaaggcct gtttcaaaag gcgattatgg agagcggtgc aagcgtgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggctt tcttcgcgcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctggcgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467

<210> SEQ ID NO 66
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 66

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30
```

```
Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Ala Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Ala Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445
```

```
Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 67
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 67

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gttttacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgtca gcattgccgc gctgctggcc    600

atgccggctg cgaaaggcct gtttcaaaag gcgattatgg agagcggtgc aagcgtgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggctt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac     960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctggtgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

<210> SEQ ID NO 68
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 68

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Val Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
```

```
        420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 69
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 69

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gttttacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgtca gcattgccgc gctgctggcc    600

atgccggctg cgaaaggcct gtttcaaaag gcgattatgg agagcggtgc aagccgtacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggttt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                        1467
```

<210> SEQ ID NO 70
<211> LENGTH: 489
<212> TYPE: PRT
<213> ORGANISM: Artificial Sequence

```
<220> FEATURE:
<223> OTHER INFORMATION: Engineered variant of B. subtilis pNB esterase

<400> SEQUENCE: 70

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Val Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400
```

```
Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 71
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 71

atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gctgtacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgtca gcattgccgc gctgctggcc    600

atgccggctg cgaaaggcct gtttcaaaag gcgattatgg agagcggtgc aagcgcgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggctt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctggcgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                        1467
```

<210> SEQ ID NO 72
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 72

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Leu Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Ala Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Ala Phe Trp Arg Pro Ala Val
        355                 360                 365
```

```
Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

```
<210> SEQ ID NO 73
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 73

atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300

gtttggattc acggcggtgc gttttacctg ggtgccggta gcgagccgct gtacgatggc     360

tccaagctgg ctgcgcaagg tgaggtcatt gtcgtcaccc tgaactatcg tctgggcccg     420

ttcggtttca tgcacctgag cagcttcgat gaggcgtata gcgacaattt gggtctgctg     480

gaccaagcga cagccctgaa atgggttcgc gagaacatca gcgcgtttgg tggcgacccg     540

gataatgtga cggtgtttgg tgaaagcgct ggtggcgtca gcattgccgc gctgctggcc     600

atgccggctg cgaaaggcct gtttcaaaag gcgattatgg agagcggtgc aagcgtgacc     660

atgaccaagg aacaagcggc gagcactgcg gcagcttttc tgcaagtgct gggtatcaat     720

gagagccagc tggatcgttt gcacaccgtc gcagcggagg acctgctgaa ggcagctgac     780

caactgcgta tcgcggagaa agagaatatc ttccaggttt tcttcgcgcc tgcactggat     840

ccgaaaactt tgccggaaga gccggaaaaa tccattgcgg aaggtgcggc aagcggtatt     900

ccgctgttga ttggtaccac gcgcgacgaa ggttacctgt ttttcacgtc tgatagcgac     960

gttcgtagcc aggaaacctt ggacgctgcg ctggagtaca gcctgggcaa gccgttggca    1020

gagaaagcgg cggacttgta cccgcgcagc ctggaatccc aaatccacat ggtgaccgat    1080

ctggtgtttt ggcgcccagc cgtggcattc gcgtctgcac agagccatta cgcaccggtg    1140

tggatgtatc gcttcgattg gcacccggag aaaccgccgt acaacaaagc cttccacgcc    1200

ctggagctgc cgtttgtttt cggtaacctg gatggcttgg aacgtatggc caaagccgaa    1260

atcacggacg aggttaagca actgtcccac acgattcaga gcgcctggat tacgtttgca    1320

aagaccggca acccgagcac cgaggcggtg aactggccgg cttatcatga agaaacccgt    1380
```

gaaaccgtga tcctggactc tgagattacc atcgagaatg accctgagag cgagaagcgt 1440
cagaagctgt tcccgagcaa gggtgaa 1467

<210> SEQ ID NO 74
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 74

Met Thr His Gln Ile Val Thr Thr Gln Tyr Gly Lys Val Lys Gly Thr
1 5 10 15

Thr Glu Asn Gly Val His Lys Trp Lys Gly Ile Pro Tyr Ala Lys Pro
20 25 30

Pro Val Gly Gln Trp Arg Phe Lys Ala Pro Glu Pro Pro Glu Val Trp
35 40 45

Glu Asp Val Leu Asp Ala Thr Ala Tyr Gly Pro Val Cys Pro Gln Pro
50 55 60

Ser Asp Leu Leu Ser Leu Ser Tyr Thr Glu Leu Pro Arg Gln Ser Glu
65 70 75 80

Asp Cys Leu Tyr Val Asn Val Phe Ala Pro Asp Thr Pro Ser Gln Asn
85 90 95

Leu Pro Val Met Val Trp Ile His Gly Gly Ala Phe Tyr Leu Gly Ala
100 105 110

Gly Ser Glu Pro Leu Tyr Asp Gly Ser Lys Leu Ala Ala Gln Gly Glu
115 120 125

Val Ile Val Val Thr Leu Asn Tyr Arg Leu Gly Pro Phe Gly Phe Met
130 135 140

His Leu Ser Ser Phe Asp Glu Ala Tyr Ser Asp Asn Leu Gly Leu Leu
145 150 155 160

Asp Gln Ala Thr Ala Leu Lys Trp Val Arg Glu Asn Ile Ser Ala Phe
165 170 175

Gly Gly Asp Pro Asp Asn Val Thr Val Phe Gly Glu Ser Ala Gly Gly
180 185 190

Val Ser Ile Ala Ala Leu Leu Ala Met Pro Ala Ala Lys Gly Leu Phe
195 200 205

Gln Lys Ala Ile Met Glu Ser Gly Ala Ser Val Thr Met Thr Lys Glu
210 215 220

Gln Ala Ala Ser Thr Ala Ala Ala Phe Leu Gln Val Leu Gly Ile Asn
225 230 235 240

Glu Ser Gln Leu Asp Arg Leu His Thr Val Ala Ala Glu Asp Leu Leu
245 250 255

Lys Ala Ala Asp Gln Leu Arg Ile Ala Glu Lys Glu Asn Ile Phe Gln
260 265 270

Val Phe Phe Ala Pro Ala Leu Asp Pro Lys Thr Leu Pro Glu Glu Pro
275 280 285

Glu Lys Ser Ile Ala Glu Gly Ala Ala Ser Gly Ile Pro Leu Leu Ile
290 295 300

Gly Thr Thr Arg Asp Glu Gly Tyr Leu Phe Phe Thr Ser Asp Ser Asp
305 310 315 320

Val Arg Ser Gln Glu Thr Leu Asp Ala Ala Leu Glu Tyr Ser Leu Gly
325 330 335

Lys Pro Leu Ala Glu Lys Ala Ala Asp Leu Tyr Pro Arg Ser Leu Glu

```
            340                 345                 350

Ser Gln Ile His Met Val Thr Asp Leu Val Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 75
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 75

atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gtattacctg ggtgccggta gccagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgtca gcattgccgc gctgctggcc    600

atgccggctg cgaaaggcct gtttcaaaag gcgattatgg agagcggtgc aagcgtgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggctt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgcaatttt ggcgcccagc cgtggcattc gcgtctgcac agagccatta cgcaccggtg   1140

tggatgtatc gcttcgattg gcacccggag aaaccgccgt acaacaaagc cttccacgcc   1200
```

```
ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467


<210> SEQ ID NO 76
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 76

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Gln Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320
```

```
Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Gln Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 77
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 77

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gttttacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgtca gcattgccgc gctgctggcc    600

atgccggctg cgaaaggcct gtttcaaaag gcgattatgg agagcggtgc aagcgtgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttcttgcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac     960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080
```

```
ctgcaatttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

```
<210> SEQ ID NO 78
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 78

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Leu Pro Ala Leu Asp Pro Lys Thr Leu Pro Glu Glu Pro
        275                 280                 285
```

```
Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Gln Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 79
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 79

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gtattacctg ggtgccggta gccagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgtca gcattgccgc gctgctggcc    600

atgccggctg cgaaaggcct gtttcaaaag gcgattatgg agagcggtgc aagcttgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggcat tcttccaacc tgcactggat    840

ccgaaaactt tgccggaaga gccggaaaaa tccattgcgg aaggtgcggc aagcggtatt    900
```

-continued

```
ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgcaatttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                        1467


<210> SEQ ID NO 80
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 80

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Gln Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Leu Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
```

```
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Gln Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485

<210> SEQ ID NO 81
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 81

atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gtattacctg ggtgccggta gccagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgata gcattgccgc gctgctggcc    600

atgccggctg cgaaaggcct gtttcaaaag gcgattatgg agagcggtgc aagcgtgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780
```

```
caactgcgta tcgcggagaa agagaatatc ttccaggctt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

```
<210> SEQ ID NO 82
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 82

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Gln Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Asp Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240
```

```
Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 83
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 83

```
atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300

gtttggattc acggcggtgc gtattacctg ggtgccggta gcgagccgct gtacgatggc     360

tccaagctgg ctgcgcaagg tgaggtcatt gtcgtcaccc tgaactatcg tctgggcccg     420

ttcggtttca tgcacctgag cagcttcgat gaggcgtata gcgacaattt gggtctgctg     480

gaccaagcgg cagccctgaa atgggttcgc gagaacatca gcgcgtttgg tggcgacccg     540

gataatgtga cggtgtttgg tgaaagcgct ggtggcgata gcattgccgc gctgctggcc     600
```

```
atgccggctg cgaaaggcct gtttcaaaag gcgattatgg agagcggtgc aagcgatacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttcttgcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc  tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                      1467
```

<210> SEQ ID NO 84
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 84

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Asp Ser Ile Ala Ala Leu Leu Ala Met Pro Ala Ala Lys Gly Leu Phe
        195                 200                 205
```

```
Gln Lys Ala Ile Met Glu Ser Gly Ala Ser Asp Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Leu Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

```
<210> SEQ ID NO 85
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 85

atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300

gtttggattc acggcggtgc gtattacctg ggtgccggta gcgagccgct gtacgatggc     360

tccaagctgg ctgcgcaagg tgaggtcatt gtcgtcaccc tgaactatcg tctgggcccg     420

ttcggtttca tgcacctgag cagcttcgat gaggcgtata gcgacaattt gggtctgctg     480
```

```
gaccaagcgg cagccctgaa atgggttcgc gagaacatca gcgcgtttgg tggcgacccg    540

gataatgtga cggtgtttgg tgaaagcgct ggtggcgaaa gcattgccgc gctgctggcc    600

atgccggctg cgaaaggcct gtttcaaaag gcgattatgg agagcggtgc aagcgatacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggctt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac     960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

<210> SEQ ID NO 86
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 86

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
```

```
            180                 185                 190

Glu Ser Ile Ala Ala Leu Leu Ala Met Pro Ala Ala Lys Gly Leu Phe
        195                 200                 205

Gln Lys Ala Ile Met Glu Ser Gly Ala Ser Asp Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

```
<210> SEQ ID NO 87
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 87

atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300
```

```
gtttggattc acggcggtgc gtattacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgata gcattgccgc gctgctggcc    600

atgccggctg cgaaaggcct gtttcaaaag gcgattatgg agagcggtgc aagcgtgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggctt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                        1467
```

```
<210> SEQ ID NO 88
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 88

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160
```

```
Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Asp Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 89
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 89

```
atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180
```

```
tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gtattacctg ggtgccggta gccagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgata gcattgccgc gctgctggcc    600

atgccggctg cgaaaggcct gtttcaaaag gcgattatgg agagcggtgc aagcgtgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggcat tcttcttgcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgtcatttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                      1467
```

<210> SEQ ID NO 90
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 90

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Gln Pro Leu Tyr Asp Gly Ser Lys Leu Ala Ala Gln Gly Glu
        115                 120                 125
```

```
Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Asp Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Leu Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Ser Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

```
<210> SEQ ID NO 91
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 91
```

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gtattacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgtca gcattgccgc gctgctggcc    600

atgccggctg cgaaaggcct gtttcaaaag gcgattatgg agagcggtgc aagcgtgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggctt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac     960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

<210> SEQ ID NO 92
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 92

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
```

```
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 93
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 93

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gtattacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgata gcattgccgc gctgctggcc    600

atgccggctg cgaaaggcct gtttcaaaag gcgattatgg agagcggtgc aagcgtgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggctt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac     960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgtcatttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

<210> SEQ ID NO 94
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 94

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80
```

```
Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Asp Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Ser Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 95
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 95

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gtattacctg ggtgccggta gccagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgata gcattgccgc gctgctggcc    600

atgccggctg cgaaaggcct gtttcaaaag gcgattatgg agagcggtgc aagcttgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggctt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac     960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgtcatttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

<210> SEQ ID NO 96
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 96

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45
```

```
Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Gln Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Asp Ser Ile Ala Ala Leu Leu Ala Met Pro Ala Ala Lys Gly Leu Phe
        195                 200                 205

Gln Lys Ala Ile Met Glu Ser Gly Ala Ser Leu Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Ser Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
```

465 470 475 480

Gln Lys Leu Phe Pro Ser Lys Gly Glu
485

<210> SEQ ID NO 97
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 97
atgacccatc aaatcgtcac cactcagtac ggcaaagtca aaggtacgac ggagaacggt 60
gttcataagt ggaaaggcat cccgtatgcg aagccgccag tgggccagtg gcgtttcaaa 120
gcgccggaac cgccggaggt ctgggaggat gttctggacg caaccgcgta tggtcctgtc 180
tgcccacagc cgtcggacct gttgagcctg agctatacgg aactgccacg tcagagcgaa 240
gattgtctgt acgttaatgt ttttgcgccg gataccccgt cccaaaatct gccggttatg 300
gtttggattc acggcggtgc gtattacctg ggtgccggta gccagccgct gtacgatggc 360
tccaagctgg ctgcgcaagg tgaggtcatt gtcgtcaccc tgaactatcg tctgggcccg 420
ttcggtttca tgcacctgag cagcttcgat gaggcgtata gcgacaattt gggtctgctg 480
gaccaagcgg cagccctgaa atgggttcgc gagaacatca gcgcgtttgg tggcgacccg 540
gataatgtga cggtgtttgg tgaaagcgct ggtggcgata gcattgccgc gctgctggcc 600
atgccggctg cgaaaggcct gtttcaaaag gcgattatgg agagcggtgc aagcgtgacc 660
atgaccaagg aacaagcggc gagcactgcg gcagcttttc tgcaagtgct gggtatcaat 720
gagagccagc tggatcgttt gcacaccgtc gcagcggagg acctgctgaa ggcagctgac 780
caactgcgta tcgcggagaa agagaatatc ttccaggctt tcttccagcc tgcactggat 840
ccgaaaactt tgccggaaga gccggaaaaa tccattgcgg aaggtgcggc aagcggtatt 900
ccgctgttga ttggtaccac gcgcgacgaa ggttacctgt tttcacgtc tgatagcgac 960 gttcgtagcc aggaaacctt ggacgctgcg ctggagtaca gcctgggcaa gccgttggca 1020
gagaaagcgg cggacttgta cccgcgcagc ctggaatccc aaatccacat ggtgaccgat 1080
ctgctgtttt ggcgcccagc cgtggcattc gcgtctgcac agagccatta cgcaccggtg 1140
tggatgtatc gcttcgattg gcacccggag aaaccgccgt acaacaaagc cttccacgcc 1200
ctggagctgc cgtttgtttt cggtaacctg gatggcttgg aacgtatggc caaagccgaa 1260
atcacggacg aggttaagca actgtcccac acgattcaga gcgcctggat tacgtttgca 1320
aagaccggca acccgagcac cgaggcggtg aactggccgg cttatcatga agaaacccgt 1380
gaaaccgtga tcctggactc tgagattacc atcgagaatg accctgagag cgagaagcgt 1440
cagaagctgt tcccgagcaa gggtgaa 1467

<210> SEQ ID NO 98
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 98

Met Thr His Gln Ile Val Thr Thr Gln Tyr Gly Lys Val Lys Gly Thr
1 5 10 15

Thr Glu Asn Gly Val His Lys Trp Lys Gly Ile Pro Tyr Ala Lys Pro

```
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Gln Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Asp Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445
```

```
Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 99
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 99

atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gtattacctg ggtgccggta gctggccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgata gcattgccgc gctgctggcc    600

atgccggctg cgaaaggcct gtttcaaaag gcgattatgg agagcggtgc aagcttgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggctt tcttcttgcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac     960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgcaatttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467


<210> SEQ ID NO 100
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 100
```

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Trp Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Asp Ser Ile Ala Ala Leu Leu Ala Met Pro Ala Ala Lys Gly Leu Phe
        195                 200                 205

Gln Lys Ala Ile Met Glu Ser Gly Ala Ser Leu Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Leu Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Gln Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415
```

```
Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 101
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 101

atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300

gtttggattc acggcggtgc gttttacctg ggtgccggta gccagccgct gtacgatggc     360

tccaagctgg ctgcgcaagg tgaggtcatt gtcgtcaccc tgaactatcg tctgggcccg     420

ttcggtttca tgcacctgag cagcttcgat gaggcgtata gcgacaattt gggtctgctg     480

gaccaagcgg cagccctgaa atgggttcgc gagaacatca gcgcgtttgg tggcgacccg     540

gataatgtga cggtgtttgg tgaaagcgct ggtggcgtca gcattgccgc gctgctggcc     600

atgccggctg cgaaaggcct gtttcaaaag gcgattatgg agagcggtgc aagcgtgacc     660

atgaccaagg aacaagcggc gagcactgcg gcagcttttc tgcaagtgct gggtatcaat     720

gagagccagc tggatcgttt gcacaccgtc gcagcggagg acctgctgaa ggcagctgac     780

caactgcgta tcgcggagaa agagaatatc ttccaggctt tcttccagcc tgcactggat     840

ccgaaaactt tgccggaaga gccggaaaaa tccattgcgg aaggtgcggc aagcggtatt     900

ccgctgttga ttggtaccac gcgcgacgaa ggttacctgt ttttcacgtc tgatagcgac     960

gttcgtagcc aggaaacctt ggacgctgcg ctggagtaca gcctgggcaa gccgttggca    1020

gagaaagcgg cggacttgta cccgcgcagc ctggaatccc aaatccacat ggtgaccgat    1080

ctgcaatttt ggcgcccagc cgtggcattc gcgtctgcac agagccatta cgcaccggtg    1140

tggatgtatc gcttcgattg gcacccggag aaaccgccgt acaacaaagc cttccacgcc    1200

ctggagctgc cgtttgtttt cggtaacctg gatggcttgg aacgtatggc caaagccgaa    1260

atcacggacg aggttaagca actgtcccac acgattcaga gcgcctggat tacgtttgca    1320

aagaccggca acccgagcac cgaggcggtg aactggccgg cttatcatga agaaacccgt    1380

gaaaccgtga tcctggactc tgagattacc atcgagaatg accctgagag cgagaagcgt    1440

cagaagctgt tcccgagcaa gggtgaa                                        1467


<210> SEQ ID NO 102
<211> LENGTH: 489
<212> TYPE: PRT
```

<213> ORGANISM: Artificial Sequence
<220> FEATURE:
<223> OTHER INFORMATION: Engineered variant of B. subtilis pNB esterase

<400> SEQUENCE: 102

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Gln Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Gln Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
```

```
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 103
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 103

atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gtattacttg ggtgccggta gctggccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgata gcattgccgc gctgctggcc    600

atgccggctg cgaaaggcct gtttcaaaag gcgattatgg agagcggtgc aagcttgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccagctgt tcttccaacc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac     960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

<210> SEQ ID NO 104
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 104

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Trp Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Asp Ser Ile Ala Ala Leu Leu Ala Met Pro Ala Ala Lys Gly Leu Phe
        195                 200                 205

Gln Lys Ala Ile Met Glu Ser Gly Ala Ser Leu Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365
```

```
Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 105
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 105

atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gtattacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgata gcattgccgc gctgctggcc    600

atgccggctg cgaaaggcct gtttcaaaag gcgattatgg agagcggtgc aagcgtgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggctt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320
```

```
aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467


<210> SEQ ID NO 106
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 106

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Asp Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335
```

```
Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 107
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 107

atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300

gtttggattc acggcggtgc gttttacctg ggtgccggta gccagccgct gtacgatggc     360

tccaagctgg ctgcgcaagg tgaggtcatt gtcgtcaccc tgaactatcg tctgggcccg     420

ttcggtttca tgcacctgag cagcttcgat gaggcgtata gcgacaattt gggtctgctg     480

gaccaagcgg cagccctgaa atgggttcgc gagaacatca gcgcgtttgg tggcgacccg     540

gataatgtga cggtgtttgg tgaaagcgct ggtggcgata gcattgccgc gctgctggcc     600

atgccggctg cgaaaggcct gtttcaaaag gcgattatgg agagcggtgc aagcttgacc     660

atgaccaagg aacaagcggc gagcactgcg gcagcttttc tgcaagtgct gggtatcaat     720

gagagccagc tggatcgttt gcacaccgtc gcagcggagg acctgctgaa ggcagctgac     780

caactgcgta tcgcggagaa agagaatatc ttccaggctt tcttcttgcc tgcactggat     840

ccgaaaactt tgccggaaga gccggaaaaa tccattgcgg aaggtgcggc aagcggtatt     900

ccgctgttga ttggtaccac gcgcgacgaa ggttacctgt ttttcacgtc tgatagcgac     960

gttcgtagcc aggaaacctt ggacgctgcg ctggagtaca gcctgggcaa gccgttggca    1020

gagaaagcgg cggacttgta cccgcgcagc ctggaatccc aaatccacat ggtgaccgat    1080

ctggactttt ggcgcccagc cgtggcattc gcgtctgcac agagccatta cgcaccggtg    1140

tggatgtatc gcttcgattg gcacccggag aaaccgccgt acaacaaagc cttccacgcc    1200
```

```
ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                        1467


<210> SEQ ID NO 108
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 108

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Gln Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Asp Ser Ile Ala Ala Leu Leu Ala Met Pro Ala Ala Lys Gly Leu Phe
        195                 200                 205

Gln Lys Ala Ile Met Glu Ser Gly Ala Ser Leu Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Leu Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
```

```
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Asp Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 109
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 109

atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gtattacctg ggtgccggta gcgagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgata gcattgccgc gctgctggcc    600

atgccggctg cgaaaggcct gtttcaaaag gcgattatgg agagcggtgc aagcttgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggctt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac     960

gttcgtagcc aggaaacctt ggacgctgcg ctggagtaca gcctgggcaa gccgttggca   1020
```

```
gagaaagcgg cggacttgta cccgcgcagc ctagaatccc aaatccacat ggtgaccgat   1080

ctgcaatttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

<210> SEQ ID NO 110
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 110

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Asp Ser Ile Ala Ala Leu Leu Ala Met Pro Ala Ala Lys Gly Leu Phe
        195                 200                 205

Gln Lys Ala Ile Met Glu Ser Gly Ala Ser Leu Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285
```

```
Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Gln Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 111
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 111

```
atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300

gtttggattc acggcggtgc gtattacctg ggtgccggta gcgagccgct gtacgatggc     360

tccaagctgg ctgcgcaagg tgaggtcatt gtcgtcaccc tgaactatcg tctgggcccg     420

ttcggtttca tgcacctgag cagcttcgat gaggcgtata gcgacaattt gggtctgctg     480

gaccaagcgg cagccctgaa atgggttcgc gagaacatca gcgcgtttgg tggcgacccg     540

gataatgtga cggtgtttgg tgaaagcgct ggtggcgtca gcattgccgc gctgctggcc     600

atgccggctg cgaaaggcct gtttcaaaag gcgattatgg agagcggtgc aagcgtgacc     660

atgaccaagg aacaagcggc gagcactgcg gcagcttttc tgcaagtgct gggtatcaat     720

gagagccagc tggatcgttt gcacaccgtc gcagcggagg acctgctgaa ggcagctgac     780

caactgcgta tcgcggagaa agagaatatc ttccaggctt tcttccagcc tgcactggat     840

ccgaaaactt tgccggaaga gccggaaaaa tccattgcgg aaggtgcggc aagcggtatt     900
```

```
ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgcaatttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

```
<210> SEQ ID NO 112
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 112

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Val Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255
```

```
Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Gln Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 113
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 113

```
atgacccatc aaatcgtcac cactcagtac ggcaaagtca aaggtacgac ggagaacggt     60

gttcataagt ggaaaggcat cccgtatgcg aagccgccag tgggccagtg gcgtttcaaa    120

gcgccggaac cgccggaggt ctgggaggat gttctggacg caaccgcgta tggtcctgtc    180

tgcccacagc cgtcggacct gttgagcctg agctatacgg aactgccacg tcagagcgaa    240

gattgtctgt acgttaatgt ttttgcgccg gataccccgt cccaaaatct gccggttatg    300

gtttggattc acggcggtgc gttttacctg ggtgccggta gctggccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgata gcattgccgc gctgctggcc    600

atgccggctg cgaaaggcct gtttcaaaag gcgattatgg agagcggtgc aagcgtgacc    660

atgaccaagg aacaagcggc gagcactgcg gcagcttttc tgcaagtgct gggtatcaat    720
```

```
gagagccagc tggatcgttt gcacaccgtc gcagcggagg acctgctgaa ggcagctgac    780

caactgcgta tcgcggagaa agagaatatc ttccaggctt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                        1467


<210> SEQ ID NO 114
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 114

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Trp Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Asp Ser Ile Ala Ala Leu Leu Ala Met Pro Ala Ala Lys Gly Leu Phe
        195                 200                 205

Gln Lys Ala Ile Met Glu Ser Gly Ala Ser Val Thr Met Thr Lys Glu
    210                 215                 220

Gln Ala Ala Ser Thr Ala Ala Ala Phe Leu Gln Val Leu Gly Ile Asn
```

```
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 115
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 115

```
atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300

gtttggattc acggcggtgc gtattacctg ggcgccggta gcgagccgct gtacgatggc     360

tccaagctgg ctgcgcaagg tgaggtcatt gtcgtcaccc tgaactatcg tctgggcccg     420

ttcggtttca tgcacctgag cagcttcgat gaggcgtata gcgacaattt gggtctgctg     480

gaccaagcgg cagccctgaa atgggttcgc gagaacatca gcgcgtttgg tggcgacccg     540

gataatgtga cggtgtttgg tgaaagcgct ggtggcgata gcattgccgc gctgctggcc     600
```

```
atgccggctg cgaaaggcct gtttcaaaag gcgattatgg agagcggtgc aagcttgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggctt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgtcatttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                       1467
```

```
<210> SEQ ID NO 116
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 116

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Asp Ser Ile Ala Ala Leu Leu Ala Met Pro Ala Ala Lys Gly Leu Phe
        195                 200                 205
```

```
Gln Lys Ala Ile Met Glu Ser Gly Ala Ser Leu Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Ser Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 117
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 117

```
atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300

gtttggattc acggcggtgc gtattacctg ggtgccggta gcgagccgct gtacgatggc     360

tccaagctgg ctgcgcaagg tgaggtcatt gtcgtcaccc tgaactatcg tctgggcccg     420
```

```
ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgata gcattgccgc gctgctggcc    600

atgccggctg cgaaaggcct gtttcaaaag gcgattatgg agagcggtgc aagcttgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggctt tcttccagcc tgcactggat    840

ccgaaaactt tgccggaaga gccggaaaaa tccattgcgg aaggtgcggc aagcggtatt    900

ccgctgttga ttggtaccac gcgcgacgaa ggttacctgt ttttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                        1467
```

<210> SEQ ID NO 118
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 118

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175
```

```
Gly Gly Asp Pro Asp Asn Val Thr Val Phe Gly Glu Ser Ala Gly Gly
            180                 185                 190

Asp Ser Ile Ala Ala Leu Leu Ala Met Pro Ala Ala Lys Gly Leu Phe
        195                 200                 205

Gln Lys Ala Ile Met Glu Ser Gly Ala Ser Leu Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485


<210> SEQ ID NO 119
<211> LENGTH: 1467
<212> TYPE: DNA
<213> ORGANISM: Artificial Sequence
<220> FEATURE:
<223> OTHER INFORMATION: Engineered variant of B. subtilis pNB esterase

<400> SEQUENCE: 119

atgacccatc aaatcgtcac cactcagtac ggcaaagtca aaggtacgac ggagaacggt      60

gttcataagt ggaaaggcat cccgtatgcg aagccgccag tgggccagtg gcgtttcaaa     120

gcgccggaac cgccggaggt ctgggaggat gttctggacg caaccgcgta tggtcctgtc     180

tgcccacagc cgtcggacct gttgagcctg agctatacgg aactgccacg tcagagcgaa     240

gattgtctgt acgttaatgt ttttgcgccg gataccccgt cccaaaatct gccggttatg     300
```

```
gtttggattc acggcggtgc gtattacctg ggtgccggta gccagccgct gtacgatggc    360

tccaagctgg ctgcgcaagg tgaggtcatt gtcgtcaccc tgaactatcg tctgggcccg    420

ttcggtttca tgcacctgag cagcttcgat gaggcgtata gcgacaattt gggtctgctg    480

gaccaagcgg cagccctgaa atgggttcgc gagaacatca gcgcgtttgg tggcgacccg    540

gataatgtga cggtgtttgg tgaaagcgct ggtggcgata gcattgccgc gctgctggcc    600

atgccggctg cgaaaggcct gtttcaaaag gcgattatgg agagcggtgc aagcttgacc    660

atgaccaagg aacaagcggc gagcactgcg gcagcttttc tgcaagtgct gggtatcaat    720

gagagccagc tggatcgttt gcacaccgtc gcagcggagg acctgctgaa ggcagctgac    780

caactgcgta tcgcggagaa agagaatatc ttccaggcat tcttcttgcc tgcactggat    840

ccgaaaactt tgccggaaga gccggaaaaa tccattgcgg aaggtgcggc aagcggtatt    900

ccgctgttga ttggtaccac gcgcgacgaa ggttacctgt tttcacgtc tgatagcgac    960

gttcgtagcc aggaaacctt ggacgctgcg ctggagtaca gcctgggcaa gccgttggca   1020

gagaaagcgg cggacttgta cccgcgcagc ctggaatccc aaatccacat ggtgaccgat   1080

ctgctgtttt ggcgcccagc cgtggcattc gcgtctgcac agagccatta cgcaccggtg   1140

tggatgtatc gcttcgattg gcacccggag aaaccgccgt acaacaaagc cttccacgcc   1200

ctggagctgc cgtttgtttt cggtaacctg gatggcttgg aacgtatggc caaagccgaa   1260

atcacggacg aggttaagca actgtcccac acgattcaga gcgcctggat tacgtttgca   1320

aagaccggca acccgagcac cgaggcggtg aactggccgg cttatcatga agaaacccgt   1380

gaaaccgtga tcctggactc tgagattacc atcgagaatg accctgagag cgagaagcgt   1440

cagaagctgt tcccgagcaa gggtgaa                                        1467


<210> SEQ ID NO 120
<211> LENGTH: 489
<212> TYPE: PRT
<213> ORGANISM: Artificial Sequence
<220> FEATURE:
<223> OTHER INFORMATION: Engineered variant of B. subtilis pNB esterase

<400> SEQUENCE: 120

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Tyr Tyr Leu Gly Ala
            100                 105                 110

Gly Ser Gln Pro Leu Tyr Asp Gly Ser Lys Leu Ala Ala Gln Gly Glu
        115                 120                 125
```

-continued

```
Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Asp Ser Ile Ala Ala Leu Leu Ala Met Pro Ala Ala Lys Gly Leu Phe
        195                 200                 205

Gln Lys Ala Ile Met Glu Ser Gly Ala Ser Leu Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Ala Phe Phe Leu Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

ENGINEERED BIOCATALYSTS USEFUL FOR CARBAPENEM SYNTHESIS

The present application is a national stage application filed under 35 USC §371 and claims priority to international application to PCT International Application No. PCT/US2014/011767, filed Jan. 16, 2014 which claims priority to co-pending U.S. Provisional Appln. Ser. No. 61/754,095, filed Jan. 18, 2013, both of which are incorporated by reference, in their entireties and for all purposes.

1. TECHNICAL FIELD

The disclosure relates to pNB esterase biocatalysts and processes using the biocatalysts for the preparation of the carbapenem antibiotic compound, imipenem.

2. REFERENCE TO SEQUENCE LISTING, TABLE OR COMPUTER PROGRAM

The official copy of the Sequence Listing is submitted concurrently with the specification as an ASCII formatted text file via EFS-Web, with a file name of "CX2-128USPI_ST25.txt", a creation date of Jan. 17, 2013, and a size of 369,801 bytes. The Sequence Listing filed via EFS-Web is part of the specification and is incorporated in its entirety by reference herein.

3. BACKGROUND

Carbapenems are a class of β-lactam antibiotics with a broad spectrum of antibacterial activity. Carbapenem antibiotics were originally developed from thienamycin, a naturally derived product of *Streptomyces cattleya*. They have a structure that is highly resistant to most β-lactamases and consequently, are often the antibiotic of last resort for treatment of highly resistant infections of bacteria such as *Escherichia coli* and *Klebsiella pneumunia*. Carbapenem antibiotics include, but are not limited to, imipenem, ertapenem, meropenem, doripenem, panipenem, biapenem, razupenem, and tabipenem.

Imipenem, (compound (1) shown below), is a carbapenem that exhibits a broad range of antibiotic activity against gram-positive and gram-negative aerobic and anaerobic bacteria species.

(1)

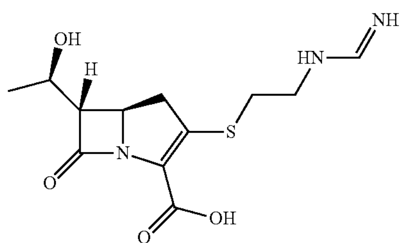

The methods of use and manufacture of imipenem were first disclosed in U.S. Pat. No. 4,194,047. Various alternative synthetic methods for the preparation of imipenem are described in e.g., U.S. Pat. Nos. 4,374,772, 4,894,450, and 7,462,712. Several synthesis routes for the preparation of imipenem include the formation of a p-nitrobenzyl-ester of imipenem (compound (2) shown below).

(2)

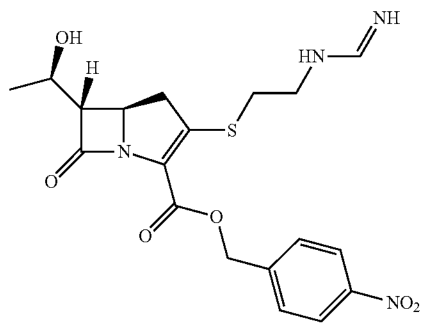

This pNB-protected imipenem of compound (2) is deprotected to provide the imipenem product of compound (1) by using palladium or platinum hydrogenation catalysts to remove the remove p-nitrobenzyl group (see e.g., U.S. Pat. Nos. 4,292,436, and 5,245,069, and U.S. Pat. Publ. 2002/0095034). The use of these catalysts for pNB deprotection, however, is expensive and results in relatively low yields of the deprotected imipenem (e.g., <60%).

The use of an esterase enzyme to remove pNB protecting groups in the synthesis of the cephalosporin-derived and 1-carba-cephalasporin antibiotics was disclosed in U.S. Pat. No. 5,468,632. A specific wild-type pNB esterase from *Bacillus subtilis* for removing such pNB protecting groups was isolated, cloned, and sequenced in U.S. Pat. No. 5,468,632. This same wild-type pNB esterase also has been engineered for increased thermostability and activity in the removal of the pNB group from a pNB-protected precursor of the antibiotic Loracarbef (see e.g., Moore et al., "Directed evolution of a para-nitrobenzyl esterase for aqueous-organic solvents," *Nature Biotechnology* 14: 458-467 (1996); Moore et al. "Strategies for the in vitro Evolution of Protein Function: Enzyme Evolution by Random Recombination of Improved Sequences." *J. Mol. Biol.* 272:336-347 (1997); Giver et al., "Directed evolution of a thermostable esterase." *Proc. Natl. Acad. Sci. USA* 95: 12809-12813 (October 1998). There remains, however, a need for an engineered pNB esterase that provides selectivity and high yields in the deprotection of pNB-protected carbapenem intermediates, such as the pNB-protected imipenem of compound (2), under commercially viable and industrially useful process conditions.

4. SUMMARY

The present disclosure provides engineered polypeptides having pNB esterase activity, polynucleotides encoding the polypeptides, methods of the making the polypeptides, and methods of using the polypeptides for the selective removal of pNB protecting groups in the synthesis of carbapenem products, such as imipenem. The engineered polypeptides having pNB esterase activity of the present disclosure have been engineered to have one or more residue differences as compared to the wild-type pNB esterase. They also have one or more residue differences as compared to the previously engineered pNB esterase polypeptide of amino acid sequence SEQ ID NO: 2, which has enhanced solvent and thermal stability relative to the wild-type pNB esterase of *Bacillus subtilis*. In particular, the engineered pNB esterase polypeptides of the present disclosure have been engineered for efficient removal a pNB protecting group from the imipenem precursor compound of compound (2) thereby converting it to the product compound (1), imipenem, as shown in Scheme 1.

Scheme 1

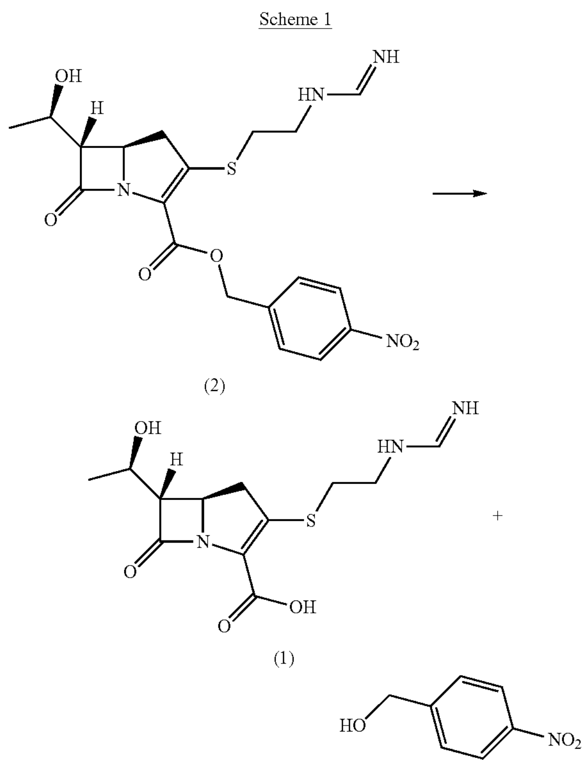

The amino residue differences are located at residue positions affecting various enzyme properties, including among others, activity, stability, product selectivity, and product tolerance. These amino residue differences, although evolved for the removal of pNB protecting groups from the imipenem precursor of compound (2), can also be used to evolve engineered pNB esterase polypeptides having activity useful for removing pNB protecting groups of structurally analogous carbapenem precursor compounds including, but not limited to, pNB-protected precursor compounds of thienamycin meropenem, doripenem, ertapenem, biopenem, and panipenem.

In one aspect, the present disclosure provides engineered polypeptides having pNB esterase activity, where the engineered polypeptide comprises an amino acid sequence having at least 80% identity to SEQ ID NO: 2 and one or more residue differences as compared to SEQ ID NO:2 at residue positions selected from: X108, X115, X116, X130, X193, X214, X219, X273, X276, X321, and X362. In some embodiments, the residue differences as compared to SEQ ID NO: 2 at the residue positions X108, X115, X116, X130, X193, X214, X219, X273, X276, X321, and X362 are selected from X108L/Y, X115Q/W, X116S, X130T, X164T, X193A/D/E/V, X214G, X219A/D/L/V, X273A/E/T/V, X276A/T/L, X321A, and X362A/D/Q/S/V.

In some embodiments, the engineered polypeptide having pNB esterase activity comprises an amino acid sequence having at least 80% identity to SEQ ID NO: 2 and one or more residue differences as compared to SEQ ID NO: 2 selected from: X108L/Y, X193A/D/E/V, X219A/D/L/V, X273A/E/T/V, and X362A/D/Q/S/V.

In some embodiments, the engineered polypeptide having pNB esterase activity comprises an amino acid sequence having at least 80% identity to SEQ ID NO: 2 and a residue difference as compared to SEQ ID NO: 2 at position X193 selected from: X193A/D/E/V. In some embodiments, the amino acid residue difference as compared to SEQ ID NO: 2 at position X193 is X193V.

In some embodiments, the engineered polypeptide having pNB esterase activity comprises an amino acid sequence having at least 80% identity to SEQ ID NO: 2, and an amino acid difference as compared to SEQ ID NO: 2 of X193V, and further comprises residue differences as compared to SEQ ID NO: 2 at positions X219 and X273 selected from X219L/V and X273A/V. In further embodiments, the amino acid sequence further comprises residue differences as compared to SEQ ID NO: 2 at positions X108 and X362 selected from X108L/Y and X362A/D/Q/S/V. In still further embodiments, the engineered polypeptide further comprises a residue difference as compared to SEQ ID NO: 2 at position X115 selected from X115Q/W.

In some embodiments, the engineered polypeptide having pNB esterase activity comprises an amino acid sequence having at least 80% identity to SEQ ID NO: 2, and a combination of residue differences as compared to SEQ ID NO: 2 selected from: (a) X193V, X219V, and X273A; (b) X108Y, X193D, X219V, X273A, and X362S; (c) X108Y, X193V, X219V, X273A, and X362Q; (d) X108Y, X115Q, X193V, X219L, X273A, and X362Q; and (e) X108Y, X115Q, X193V, X219V, X273A, and X362Q.

In some embodiments, the engineered polypeptides having pNB esterase activity disclosed above (and elsewhere herein) can have additional residue differences at other residue positions. In some embodiments, the engineered pNB esterases can have 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 additional residue differences as compared to SEQ ID NO:2. In some embodiments, the engineered pNB esterases can have 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 additional residue differences. In some embodiments, the amino acid sequence has additionally 1, 2, 3, 4, 5, 6, 7, 8, 9, 10, 11, 12, 13, 14, 15, 16, 18, 20, 21, 22, 23, 24, or 25 residue differences as compared to SEQ ID NO: 2.

In some embodiments, the engineered polypeptide having pNB esterase activity comprises an amino acid sequence having at least 80% identity to SEQ ID NO: 2, one or more amino acid residue difference as compared to SEQ ID NO: 2 selected from X108L/Y, X115Q/W, X193A/D/E/V, X219A/D/L/V, X273A/E/T/V, and X362A/D/Q/S/V, and the amino acid sequence further comprises one or more residue differences as compared to SEQ ID NO: 2 selected from: X116S, X130T, X164T, X214G, X276A/T/L, and X321A. In still further embodiments, the amino acid sequence can further comprise a residue difference as compared to SEQ ID NO: 2 selected from: X49G, X94G, X96S, X227T, X251V, X267R, X271L, X274L. X313F, X322C/Y, X343V, X356R, X359A, X398L, X412E, X437T, X464A, and X481R.

In some embodiments, the engineered polypeptide having pNB-esterase activity comprises an amino acid sequence having at least 80% identity to SEQ ID NO: 2, and of any of the amino acid differences as compared to SEQ ID NO: 2 as disclosed herein (e.g., as disclosed in the exemplary polypeptides of Table 2), but in which the amino acid sequence does not comprise a residue difference as compared to SEQ ID NO: 2 at positions X60, X144. X317, X322, X334, X358, and X370.

In some embodiments, the engineered polypeptides having pNB esterase activity of the present disclosure having at least 80% identity to SEQ ID NO: 2 and any of the amino acid residue differences disclosed herein, further comprises at least 1.2 fold, 2 fold, 5 fold, 10 fold, 20 fold, 25 fold, 50 fold, 75 fold, 100 fold, or greater increased activity as compared to the polypeptide of SEQ ID NO: 4 in converting compound (2) to compound (1) under suitable reaction conditions.

In some embodiments, the engineered polypeptides having pNB esterase activity comprises an amino acid sequence having at least 80%, 85%, 87%, 88%, 89%, 90% 91%, 92%, 93%, 94%, 95%, 96%, 97%, 98%, 99%, or 100% identity to a sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120.

In some embodiments, that disclosure further provides any of the engineered polypeptides having pNB esterase activity as disclosed herein, wherein the polypeptide is immobilized on a solid support. In some embodiments, the solid support is a bead or resin comprising polymethacrylate with epoxide functional groups, polymethacrylate with amino epoxide functional groups, styrene/DVB copolymer or polymethacrylate with octadecyl functional groups Exemplary engineered polypeptides having pNB esterase activity and amino acid sequences incorporating the residue differences disclosed herein, including various combinations thereof, and having improved properties (e.g., capable of converting compound (2) to compound (1) under suitable reaction conditions) are disclosed in Table 2, and the Examples. The amino acid sequences are provided in the Sequence Listing and include SEQ ID NO: 4, 6, 8, 10, 12, 14, 16, 18, 20, 22, 24, 26, 28, 30, 32, 34, 36, 38.40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120.

In another aspect, the present disclosure provides polynucleotides encoding the engineered polypeptides having pNB esterase activity, as well as expression vectors comprising the polynucleotides, and host cells capable of expressing the polynucleotides encoding the engineered polypeptides. Exemplary polynucleotide sequences are provided in the Sequence Listing incorporated by reference herein and include SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, and 119.

In some embodiments, the present disclosure also provides methods of manufacturing the engineered polypeptides having pNB esterase activity, where the method can comprise culturing a host cell capable of expressing a polynucleotide encoding the engineered polypeptide under conditions suitable for expression of the polypeptide. In some embodiments, the method for manufacturing the engineered pNB esterase polypeptide can also include: (a) synthesizing a polynucleotide encoding a polypeptide comprising an amino acid sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120, and having one or more residue differences as compared to SEQ ID NO:2 at residue positions X108, X115, X116, X130, X193, X214, X219, X273, X276, X321, and X362 selected from X108L/Y, X115Q/W, X116S, X130T, X164T, X193A/D/E/V, X214G, X219A/D/L/V, X273A/E/T/V, X276A/T/L, X321A, and X362A/D/Q/S/V; and (b) expressing the pNB esterase polypeptide encoded by the polynucleotide. As further provided in the detailed description, additional variations can be incorporated during the synthesis of the polynucleotide to prepare engineered polypeptides with corresponding differences in the expressed amino acid sequences.

The structural features of the engineered pNB esterase polypeptides allow for the conversion of the pNB-protected substrate of compound (2) to their corresponding un-protected product of compound (1), imipenem. Thus, in another aspect the present disclosure provides a process for preparing carbapenem antibiotic of compound (1), imipenem, or a salt or hydrate of compound (1),

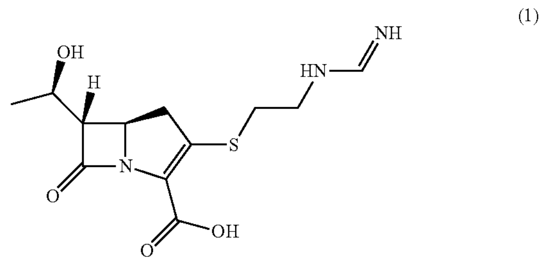 [SMILES: C[C@@H](O)[C@H]1C(=O)N2C(C(=O)O)=C(SCCNC=N)C[C@H]12]

wherein the method comprises contacting a substrate compound (2), or a salt of hydrate of compound (2),

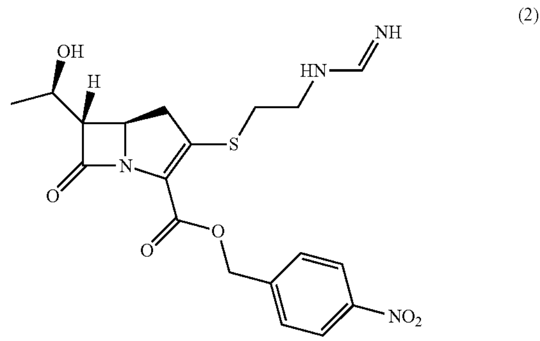 [SMILES: C[C@@H](O)[C@H]1C(=O)N2C(C(=O)OCc3ccc([N+](=O)[O-])cc3)=C(SCCNC=N)C[C@H]12]

with an engineered pNB esterase polypeptide of the present disclosure, under suitable reaction conditions. As provided herein, the processes using the engineered pNB esterases can be carried out under a range of suitable reaction conditions, including, among others, pH, temperature, buffer, solvent system, substrate loading, polypeptide loading, cofactor loading, pressure, and reaction time. In some embodiments, the suitable reaction conditions for a biocatalytic process using the engineered pNB esterases of the present disclosure can comprise: (a) substrate loading at about 2 g/L to 200 g/L; (b) about 0.1 to 10 g/L of engineered pNB esterase polypeptide; (c) about 0.05 to 0.5 M MES buffer; (d) about 5% to about 20% (v/v) DMF co-solvent; (e) pH of about 6 to 8; and/or (f) temperature of about 10 to 35° C. Further, guidance on the choice of engineered pNB esterases, preparation of the biocatalysts, and parameters and reaction conditions for carrying out the processes are described in the detailed description that follow.

5. DETAILED DESCRIPTION

As used in this specification and the appended claims, the singular forms “a”, “an” and “the” include plural referents unless the context clearly indicates otherwise. Thus, for example, reference to "a polypeptide" includes more than one polypeptide. Similarly, "comprise," "comprises," "comprising" "include," "includes," and "including" are interchangeable and not intended to be limiting. It is to be further understood that where descriptions of various embodiments use the term "comprising," those skilled in the art would understand that in some instances, the embodiment can be alternatively described using the terms "consisting essentially of" or "consisting of."

It is to be understood that both the foregoing general description, and the following detailed description are exemplary and explanatory only and are not restrictive of this disclosure. The section headings used herein are for organizational purposes only and not to be construed as limiting the subject matter described.

5.1 Abbreviations

The abbreviations used for the genetically encoded amino acids are conventional and are as follows:

| Amino Add | Three-Letter Abbreviation | One-Letter Abbreviation |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | HIS | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When the three-letter abbreviations are used, unless specifically preceded by an "L" or a "D" or clear from the context in which the abbreviation is used, the amino acid may be in either the L- or D-configuration about α-carbon ($C_\alpha$). For example, whereas "Ala" designates alanine without specifying the configuration about the α-carbon, "D-Ala" and "L-Ala" designate D-alanine and L-alanine, respectively. When the one-letter abbreviations are used, upper case letters designate amino acids in the L-configuration about the α-carbon and lower case letters designate amino acids in the D-configuration about the α-carbon. For example, "A" designates L-alanine and "a" designates D-alanine. When polypeptide sequences are presented as a string of one-letter or three-letter abbreviations (or mixtures thereof), the sequences are presented in the amino (N) to carboxy (C) direction in accordance with common convention.

The abbreviations used for the genetically encoding nucleosides are conventional and are as follows: adenosine (A); guanosine (G); cytidine (C); thymidine (T); and uridine (U). Unless specifically delineated, the abbreviated nucleotides may be either ribonucleosides or 2'-deoxyribonucleosides. The nucleosides may be specified as being either ribonucleosides or 2'-deoxyribonucleosides on an individual basis or on an aggregate basis. When nucleic acid sequences are presented as a string of one-letter abbreviations, the sequences are presented in the 5' to 3' direction in accordance with common convention, and the phosphates are not indicated.

5.2 Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings.

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Polynucleotide" or "nucleic acid" refers to two or more nucleosides that are covalently linked together. The polynucleotide may be wholly comprised ribonucleosides (i.e., an RNA), wholly comprised of 2'-deoxyribonucleotides (i.e., a DNA) or mixtures of ribo- and 2'-deoxyribonucleosides. While the nucleosides will typically be linked together via standard phosphodiester linkages, the polynucleotides may include one or more non-standard linkages. The polynucleotide may be single-stranded or double-stranded, or may include both single-stranded regions and double-stranded regions. Moreover, while a polynucleotide will typically be composed of the naturally occurring encoding nucleobases (i.e., adenine, guanine, uracil, thymine and cytosine), it may include one or more modified and/or synthetic nucleobases, such as, for example, inosine, xanthine, hypoxanthine, etc. Preferably, such modified or synthetic nucleobases will be encoding nucleobases.

"pNB esterase activity" as used herein refers to the enzymatic activity of hydrolyzing a para-nitrobenzyl ester group to form para-nitrophenol and the corresponding acid of the ester.

"pNB esterase" as used herein refers to an enzyme having pNB esterase activity and can include a naturally occurring (wild-type) pNB esterase, such as the pNB esterase from *Bacillus subtilis*, as well as non-naturally occurring engineered pNB esterase polypeptides generated by human manipulation.

"Coding sequence" refers to that portion of a nucleic acid (e.g., a gene) that encodes an amino acid sequence of a protein.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" or "engineered" or "non-naturally occurring" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch. 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc. Natl. Acad. Sci. USA 89:10915). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity. In some embodiments, a "reference sequence" can be based on a primary amino acid sequence, where the reference sequence is a sequence that can have one or more changes in the primary sequence. For instance, a "reference sequence based on SEQ ID NO:2 having at the residue corresponding to X193 an alanine" or "X193A" refers to a reference sequence of SEQ ID NO:2 in which the corresponding residue at X193 (which is a methionine in SEQ ID NO:2), has been changed to alanine.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent identity and 89 to 95 percent sequence identity, more usually at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered pNB esterase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Amino acid difference" or "residue difference" refers to a change in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X193 as compared to SEQ ID NO: 2" refers to a change of the amino acid residue at the polypeptide position corresponding to position 193 of SEQ ID NO:2. Thus, if the reference polypeptide of SEQ ID NO: 2 has a methionine at position 193, then a "residue difference at position X193 as compared to SEQ ID NO:2" an amino acid substitution of any residue other than methionine at the position of the polypeptide corresponding to position 193 of SEQ ID NO: 2. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some embodiments, where more than one amino acid can appear in a specified residue position, the alternative amino acids can be listed in the form XnY/Z, where Y and Z represent alternate amino acid residues. In some instances (e.g., in Table 2), the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. Furthermore, in some instances, a polypeptide of the present disclosure can include one or more amino acid residue differences relative to a reference sequence, which is indicated by a list of the specified positions where changes are made relative to the reference sequence.

"Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acid having aromatic side chains is substituted with another amino acid having an aromatic side chain, e.g., phenylalanine, tyrosine, tryptophan, and histidine; an amino acid with a basic side chain is substituted with another amino acid with a basic side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively. Exemplary conservative substitutions are provided in Table 1 below.

TABLE 1

| Residue | Possible Conservative Substitutions |
|---|---|
| A, L, V, I | Other aliphatic (A, L, V, I)<br>Other non-polar (A, L, V, I, G, M) |
| G, M | Other non-polar (A, L, V, I, G, M) |
| D, E | Other acidic (D, E) |
| K, R | Other basic (K, R) |
| N, Q, S, T | Other polar |
| H, Y, W, F | Other aromatic (H, Y, W, F) |
| C, P | None |

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine), (b) the charge or hydrophobicity, or (c) the bulk of the side chain. By way of example and not limitation, an exemplary non-conservative substitution can be an acidic amino acid substituted with a basic or aliphatic amino acid, an aromatic amino acid substituted with a small amino acid; and a hydrophilic amino acid substituted with a hydrophobic amino acid.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered pNB esterase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the improved engineered pNB esterase enzymes comprise insertions of one or more amino acids to the naturally occurring pNB esterase polypeptide as well as insertions of one or more amino acids to other improved pNB esterase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the reference polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of the full-length pNB esterase polypeptide, for example the reference engineered pNB esterase polypeptide of SEQ ID NO: 2.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved pNB esterase enzymes may be present within a cell, present in the cellular medium, or prepared in various forms, such as lysates or isolated preparations. As such, in some embodiments, the improved pNB esterase enzyme can be an isolated polypeptide.

"Substantially pure polypeptide" refers to a composition in which the polypeptide species is the predominant species present (i.e., on a molar or weight basis, it is more abundant than any other individual macromolecular species in the composition), and is generally a substantially purified composition when the object species comprises at least about 50 percent of the macromolecular species present by mole or % weight. Generally, a substantially pure pNB esterase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved pNB esterase polypeptide is a substantially pure polypeptide composition.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.c.).

Enantiomeric excess and diastereomeric excess are types of stereomeric excess. "Improved enzyme property" refers to a pNB esterase polypeptide that exhibits an improvement in any enzyme property as compared to a reference pNB esterase. For the engineered pNB esterase polypeptides described herein, the comparison is generally made to the reference engineered pNB esterase enzyme of SEQ ID NO: 4, although in some embodiments, the reference pNB esterase can be another engineered pNB esterase, or the wild-type pNB esterase of *B. subtilis*. Enzyme properties for which improvement is desirable include, but are not limited to, enzymatic activity (which can be expressed in terms of percent conversion of the substrate), thermostability, solvent stability, product selectivity, pH activity profile, refractoriness to inhibitors (e.g., substrate or product inhibition), and stereoselectivity (including enantioselectivity).

"Increased enzymatic activity" refers to an improved property of the engineered pNB esterase polypeptides, which can be represented by an increased specific activity (e.g., product produced/time/weight protein) or an increased percent conversion of the substrate to the product (e.g., percent conversion of starting amount of substrate to product in a specified time period using a specified amount of pNB esterase) as compared to the reference pNB esterase enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.2 fold the enzymatic activity of the corresponding wild-type pNB esterase enzyme, to as much as 2 fold, 5 fold, 10 fold, 20 fold, 25 fold, 50 fold, 75 fold, 100 fold, or more enzymatic activity than the naturally occurring pNB esterase or another engineered pNB esterase from which the pNB esterase polypeptides were derived. PNB esterase activity can be measured by any one of standard assays, such as by monitoring changes in spectrophotometric properties of reactants or products. In some embodiments, the amount of products produced can be measured by High-Performance Liquid Chromatography (HPLC) separation combined with UV absorbance or fluorescent detection following derivatization, such as with o-phthaldialdehyde (OPA). Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

"Conversion" refers to the enzymatic conversion of the substrate(s) to the corresponding product(s). "Percent conversion" refers to the percent of the substrate that is converted to the product within a period of time under specified conditions. Thus, the "enzymatic activity" or "activity" of a pNB esterase polypeptide can be expressed as "percent conversion" of the substrate to the product.

"Thermostable" refers to a pNB esterase polypeptide that maintains similar activity (more than 60% to 80% for example) after exposure to elevated temperatures (e.g., 40-80° C.) for a period of time (e.g., 0.5-24 hrs) compared to the wild-type enzyme.

"Solvent stable" refers to a pNB esterase polypeptide that maintains similar activity (more than e.g., 60% to 80%) after exposure to varying concentrations (e.g., 5-99%) of solvent (ethanol, isopropyl alcohol, dimethylsulfoxide (DMSO), tetrahydrofuran, 2-methyltetrahydrofuran, acetone, toluene, butyl acetate, methyl tert-butyl ether, etc.) for a period of time (e.g., 0.5-24 hrs) compared to the wild-type enzyme.

"Thermo- and solvent stable" refers to a pNB esterase polypeptide that is both thermostable and solvent stable.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ion strength, temperature, G/C content, and the presence of chaotropic agents. The $T_m$ values for polynucleotides can be calculated using known methods for predicting melting temperatures (see, e.g., Baldino et al., Methods Enzymology 168:761-777; Bolton et al., 1962, Proc. Natl. Acad. Sci. USA 48:1390; Bresslauer et al., 1986, Proc. Natl. Acad. Sci. USA 83:8893-8897; Freier et al., 1986, Proc. Natl. Acad. Sci. USA 83:9373-9377; Kierzek et al., Biochemistry 25:7840-

7846; Rychlik et al., 1990, Nucleic Acids Res 18:6409-6412 (erratum, 1991, Nucleic Acids Res 19:698); Sambrook et al., supra); Suggs et al., 1981, In Developmental Biology Using Purified Genes (Brown et al., eds.), pp. 683-693, Academic Press; and Wetmur, 1991, Crit Rev Biochem Mol Biol 26:227-259. All publications incorporated herein by reference). In some embodiments, the polynucleotide encodes the polypeptide disclosed herein and hybridizes under defined conditions, such as moderately stringent or highly stringent conditions, to the complement of a sequence encoding an engineered pNB esterase enzyme of the present disclosure.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide. 5× Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5× Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the pNB esterase enzymes may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package: CodonW, John Peden, University of Nottingham; McInerney, J. O, 1998, Bioinformatics 14:372-73; Stenico et al., 1994, Nucleic Acids Res. 222437-46; Wright. F., 1990, Gene 87:23-29). Codon usage tables are available for a growing list of organisms (see for example, Wada et al., 1992, Nucleic Acids Res. 20:2111-2118; Nakamura et al., 2000, Nucl. Acids Res. 28:292; Duret, et al., supra; Henaut and Danchin, "*Escherichia coli* and *Salmonella,*" 1996, Neidhardt, et al. Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., Bioinformatics: Sequence and Genome Analysis, Chapter 8, Cold Spring Harbor Laboratory Press, Cold Spring Harbor, N.Y., 2001; Uberbacher, E. C., 1996, Methods Enzymol. 266:259-281; Tiwari et al., 1997, Comput. Appl. Biosci. 13:263-270).

"Control sequence" is defined herein to include all components, which are necessary or advantageous for the expression of a polynucleotide and/or polypeptide of the present disclosure. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" refers to a nucleic acid sequence that is recognized by a host cell for expression of a polynucleotide of interest, such as a coding sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Suitable reaction conditions" refer to those conditions in the biocatalytic reaction solution (e.g., ranges of enzyme loading, substrate loading, cofactor loading, temperature, pH, buffers, co-solvents, etc.) under which a pNB esterase polypeptide of the present disclosure is capable of converting a substrate compound to a product compound (e.g., conversion of compound (2) to compound (1)). Exemplary "suitable reaction conditions" are provided in the detailed description and illustrated by the Examples.

"Loading", such as in "compound loading" or "enzyme loading" or "cofactor loading" refers to the concentration or amount of a component in a reaction mixture at the start of the reaction.

"Substrate" in the context of a biocatalyst mediated process refers to the compound or molecule acted on by the biocatalyst. For example, an exemplary substrate for the engineered pNB esterase biocatalysts in the process disclosed herein is compound (2).

"Product" in the context of a biocatalyst mediated process refers to the compound or molecule resulting from the action of the biocatalyst. For example, an exemplary product for the engineered pNB esterase biocatalysts in the process disclosed herein is compound (1).

"Protecting group" refers to a group of atoms that mask, reduce or prevent the reactivity of the functional group when attached to a reactive functional group in a molecule. Typically, a protecting group may be selectively removed as desired during the course of a synthesis. Examples of protecting groups can be found in Wuts and Greene, "Greene's Protective Groups in Organic Synthesis," 4$^{th}$ Ed., Wiley Interscience (2006), and Harrison et al., Compendium of Synthetic Organic Methods, Vols. 1-8, 1971-1996, John Wiley & Sons, NY. Functional groups that can have a protecting group include, but are not limited to, hydroxy, amino, and carboxy groups.

5.3 Engineered pNB Esterase Polypeptides

The present disclosure provides engineered polypeptides having pNB esterase activity, polynucleotides encoding the polypeptides, and methods for using the polypeptides. Where the foregoing description relates to polypeptides, it is to be understood that it also describes the polynucleotides encoding the polypeptides.

The present disclosure relates to engineered pNB esterase polypeptides derived from the wild-type pNB esterase polypeptide of *Bacillus subtilis* of GenBank Access. No.: AAA81915.1, GI:468046. The engineered pNB esterases of the present disclosure have been engineered with amino acid residue substitutions that allow for conversion of a pNB-protected substrate of compound (2) to the corresponding deprotected product of compound (1), imipenem. Significantly, the present disclosure identifies amino acid residue positions and corresponding amino acid residue substitutions in the engineered pNB esterase polypeptide that can increase the enzymatic activity, product selectivity, and stability, in deprotecting pNB-protected carbapenem substrates.

The identification of the specific residue positions and substitutions in the engineered pNB esterase polypeptides of the present disclosure by engineering through directed evolution methods using structure-based rational sequence library design with screening for improved functional properties using an activity assay based on the conversion of the pNB-protected imipenem precursor of compound (2) to its corresponding unprotected product of compound (1), imipenem. Specifically, the conversion of substrate compound (2) to product compound (1) as shown in Scheme 1 (above). The engineered pNB esterase polypeptides of the present disclosure were evolved to efficiently convert the pNB-protected imipenem substrate of compound (2) to the product compound (1), under suitable reaction conditions.

The specific structural features and structure-function correlating information of the engineered pNB esterase polypeptides of the present disclosure also allow for the rational design and directed evolution of engineered pNB esterase polypeptides that can carry out the selective deprotection of other pNB-protected carbapenem compounds (other than compound (2)), to the corresponding carbapenem product compound (other than compound (1)). In some embodiments, the engineered pNB esterase polypeptides of the present disclosure are capable of converting pNB-protected carbapenem compounds which are structural analogs of compound (2), to their corresponding deprotected carbapenem product compounds which are structural analogs of compound (1).

The engineered pNB esterase polypeptides adapted for efficient conversion of compound (2) to compound (1) have one or more residue differences as compared to the amino acid sequence of the reference engineered pNB esterase polypeptide of SEQ ID NO: 2. The residue differences are associated with enhancements in enzyme properties, including enzymatic activity, enzyme stability, and resistance to formation of undesirable side-products, such as a β-lactam ring-opened diacid of compound (3).

(3)

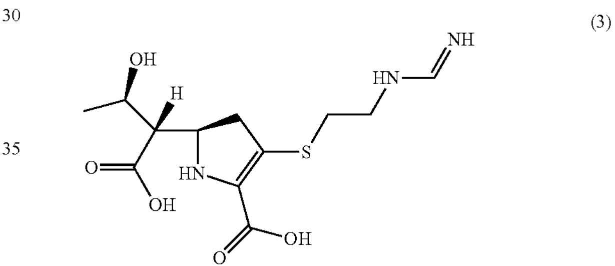

In some embodiments, the engineered pNB esterase polypeptides show increased activity in the conversion of pNB-protected substrate compound (2) to the deprotected product compound (1) in a defined time with the same amount of enzyme as compared to the reference engineered pNB esterase of SEQ ID NO: 4. In some embodiments, the engineered pNB esterase polypeptide has at least about 1.2 fold, 1.5 fold, 2 fold, 3 fold, 4 fold, 5 fold, 10 fold, 20 fold, 30 fold, 40 fold, or 50 fold or more the activity as compared to the reference engineered polypeptide represented by SEQ ID NO:4 under suitable reaction conditions.

In some embodiments, the engineered pNB esterase polypeptides are capable of converting substrate compound (2) to product compound (1) with increased tolerance for the presence of substrate relative to the reference polypeptide of SEQ ID NO: 4 under suitable reaction conditions. Thus, in some embodiments the engineered pNB esterase polypeptides are capable of converting the substrate compound (2) to product compound (1) under a substrate loading concentration of at least about 1 g/L, about 5 g/L, about 10 g/L, about 20 g/L, about 30 g/L, about 40 g/L, about 50 g/L, about 70 g/L, about 100 g/L, about 125 g/L, about 150 g/L, about 175 g/L or about 200 g/L or more with a percent conversion of at least about at least about 50%, at least about 60%, at least about 70%, at least about 80%, at least about 90%, at least about 95%, at least about 98%, or at least about 99%, in a reaction time of about 72 h or less, about 48 h or less, about 36 h or less, or about 24 h less, under suitable reaction conditions.

In some embodiments, the engineered pNB esterase polypeptides are capable of converting at least 70% of substrate compound (2) to product compound (1) in 2 h, at a substrate loading of 25 g/L and a temperature of 15° C.

In some embodiments, the engineered pNB esterase polypeptides are capable of converting substrate compound (2) to product compound (1) with a selectivity ratio for product compound (1) to side-product compound (3) of at least 50:1, at least 60:1, at least 70:1, at least 80:1, at least 90:1, or greater.

The suitable reaction conditions under which the above-described improved properties of the engineered polypeptides carry out the conversion can be determined with respect to concentrations or amounts of polypeptide, substrate, buffer, co-solvent, pH, and/or conditions including temperature and reaction time, as further described below and in the Examples.

The present disclosure provides 59 exemplary engineered pNB esterase polypeptides having structural features capable of converting the substrate of compound (2), a pNB-protected precursor of imipenem, to the corresponding product of compound (1), imipenem. The present disclosure provides the sequence structure of the 59 exemplary engineered pNB esterase polypeptides as SEQ ID NOs: 3-120 in the electronic Sequence Listing file accompanying this disclosure, which is hereby incorporated by reference herein. The odd numbered sequence identifiers (i.e., SEQ ID NOs) refer to the nucleotide sequence encoding the amino acid sequence provided by the even numbered SEQ ID NOs. The present disclosure also provides in Table 2 sequence structural information correlating specific amino acid sequence features with the functional activity of the engineered pNB esterase polypeptides. This structure-function correlation information is provided in the form of specific amino acid residues differences relative to the reference engineered polypeptide of SEQ ID NO: 2 and associated experimentally determined activity data for the 59 exemplary engineered pNB esterases of SEQ ID NOs: 3-120. The amino acid residue differences are based on comparison to the reference sequence of SEQ ID NO: 2, which has the following 7 amino acid residue differences relative to the sequence of the wild-type pNB-esterase from *Bacillus subtilis* (GenBank Access. No.: AAA81915.1, GI:468046): 160V, L144M, P317S, H322R, L334S, M358V, and Y370F. As noted in Table 2, the engineered polypeptide of SEQ ID NO: 2 does not have detectable activity in the conversion of compound (2) to compound (1). The engineered pNB esterase polypeptide of SEQ ID NO: 4 which has the single amino acid difference M193A as compared to SEQ ID NO: 2 was found to have detectable activity in the conversion of compound (2) to compound (1). It was used as the reference for the relative activity measurements. The relative pNB esterase activity of each exemplary engineered pNB esterase polypeptide was determined as conversion of the substrate compound (2) to the imipenem product of compound (1) in comparison to the pNB esterase activity of the engineered pNB esterase polypeptide of SEQ ID NO: 4 over a set time period and temperature in a high-throughput (HTP) assay. The Activity Improvement values in Table 2 were determined using an assay of *E. coli* clear cell lysates in 96 well-plate format of ~250 μL volume per well following assay reaction conditions as noted in the table and the Examples.

TABLE 2

Engineered pNB Esterase Polypeptides and Relative Activity Improvement

| SEQ ID NO: (nt/aa) | Amino Acid Differences (relative to SEQ ID NO: 2) | Activity Improvement (relative to SEQ ID NO: 4) |
|---|---|---|
| 1/2 | None | not detected |
| 3/4 | M193A; | 1 |
| 5/6 | F108Y; P116S; M193A; | 1.4 |
| 7/8 | F108Y; M193A; | 1.8 |
| 9/10 | E115W; M193A; | 1.0 |
| 11/12 | E115Q; M193A; | 1.2 |
| 13/14 | M193V; E214G; | 4.3 |
| 15/16 | M193A; R219D; | 9.5 |
| 17/18 | M193A; R219L; | 3.8 |
| 19/20 | M193A; L273E; | 12.1 |
| 21/22 | M193A; Q276H; | 10.4 |
| 23/24 | M193A; Q276T; | 3.2 |
| 25/26 | M193A; Q276L; | 7.9 |
| 27/28 | I130T; M193A; Q276H; | 10.4 |
| 29/30 | M193A; L362D; | 13.9 |
| 31/32 | M193A; L362S; | 1.6 |
| 33/34 | M193A; L362Q; | 6.9 |
| 35/36 | M193E; | 48.1 |
| 37/38 | M193D; | 7.2 |
| 39/40 | F108L; M193V; | 7.4 |
| 41/42 | M193V; L273V; Q276A; | 15.7 |
| 43/44 | M193V; R219V; L273V; Q276A; L362V; | 8.9 |
| 45/46 | F108L; M193A; R219V; L273V; | 19.9 |
| 47/48 | F108L; R219V; L273V; | 10.0 |
| 49/50 | M193V; L273V; Q276A; L362A; | 14.0 |
| 51/52 | M193V; R219A; L273V; L362V; | 22.0 |
| 53/54 | M193V; R219V; L273A; | 47.2 |
| 55/56 | M193V; L273A; Q276A; V321A; L362A; | 13.5 |
| 57/58 | M193V; R219A; L273A; Q276A; L362V; | 9.9 |
| 59/60 | F108L; R219V; L362A; | 9.6 |
| 61/62 | F108L; R219V; L362V; | 14.0 |
| 63/64 | F108L; M193V; L273A; L362A; | 16.1 |
| 65/66 | M193V; R219V; L273A; Q276A; L362A; | 20.5 |

TABLE 2-continued

| Engineered pNB Esterase Polypeptides and Relative Activity Improvement | | |
|---|---|---|
| SEQ ID NO: (nt/aa) | Amino Acid Differences (relative to SEQ ID NO: 2) | Activity Improvement (relative to SEQ ID NO: 4) |
| 67/68 | M193V; R219V; L273A; L362V; | 13.2 |
| 69/70 | M193V; L273V; | 20.5 |
| 71/72 | F108L; M193V; R219A; L273A; L362A; | 13.0 |
| 73/74 | A164T; M193V; R219V; L273V; Q276A; L362V; | 9.2 |
| 75/76 | F108Y; E115Q; M193V; R219V; L273A; L362Q; | 247 |
| 77/78 | M193V; R219V; Q276L; L362Q; | 119 |
| 79/80 | F108Y; E115Q; M193V; R219L; L273A; L362Q; | 239 |
| 81/82 | F108Y; E115Q; M193D; R219V; L273A; | 143 |
| 83/84 | F108Y; M193D; R219D; Q276L; | 76 |
| 85/86 | F108Y; M193E; R219D; | 47 |
| 87/88 | F108Y; M193D; R219V; L273A; | 220 |
| 89/90 | F108Y; E115Q; M193D; R219V; L273A; Q276L; L362S; | 204 |
| 91/92 | F108Y; M193V; R219V; L273A; | 122 |
| 93/94 | F108Y; M193D; R219V; L273A; L362S; | 205 |
| 95/96 | F108Y; E115Q; M193D; R219L; L273A; L362S; | 43 |
| 97/98 | F108Y, E115Q; M193D; R219V; L273A; | 174 |
| 99/100 | F108Y; E115W; M193D; R219L; L273A Q276L; L362Q; | 92 |
| 101/102 | E115Q; M193V; R219V; L273A; L362Q; | 172 |
| 103/104 | F108Y; E115W; M193D; R219L; | 152 |
| 105/106 | F108Y, M193D; R219V; L273A; | 174 |
| 107/108 | E115Q; M193D; R219L; L273A; Q276L; L362D; | 161 |
| 109/110 | F108Y; M393D; R219L; L273A; L362Q; | 185 |
| 111/112 | F108Y; M193V; R219V; L273A; L362Q; | 186 |
| 113/114 | E115W; M193D; R219V; L273A; | 186 |
| 115/116 | F108Y; M193D; R219L; L273A; L362S; | 232 |
| 117/118 | F108Y; M193D; R219L; L273A | 186 |
| 119/120 | F108Y; E115Q; M193D; R219L; L273A; Q276L; | 166 |

[1]Activity Improvement (relative to SEQ ID NO: 4) is calculated as the ratio of % conversion of product formed by the engineered pNB-esterase polypeptide of interest to the % conversion of the reference polypeptide of SEQ ID NO: 4 under Reaction Conditions A. % Conversion was quantified by dividing the areas of the product peak by the sum of the areas of the substrate and product peak as determined by HPLC analysis.
Reaction Conditions A: 2 g/L substrate of compound (2). 125 μL lysate (prepared by adding 200 μL of Lysis Buffer (1 mg/mL lysozyme, 0.5 mg/mL polymyxin B sulfate, 0.1M phosphate buffer, pH 7.5) to *E. coli* expressing polypeptide of interest grown in 96 well plates), 0.1M phosphate buffer. pH 7.5, 15% (v/v) DMF, 15° C., 2 h. Total reaction volume is 200 μL.

From an inspection of the amino acid sequences, and results for the 59 exemplary engineered pNB esterase polypeptides of Table 2, improved properties of increased activity, selectivity, and/or stability, that are associated with one or more residue differences as compared to SEQ ID NO: 2 at the following residue positions: X108, X115, X116, X130, X193, X214, X219, X273, X276, X321, and X362. The specific amino acid differences as compared to SEQ ID NO: 2 at each of these positions that are associated with the improved properties include X108L/Y, X115Q/W, X116S, X130T, X164T, X193A/D/E/V, X214G, X219A/D/L/V, X273A/E/T/V, X276A/T/L, X321A, and X362A/D/Q/S/V.

In some embodiments, the engineered pNB esterase polypeptides of the present disclosure comprise amino acid sequences having residue differences as compared to the engineered pNB esterase represented by SEQ ID NO:2 at residue positions selected from: X108, X115, X116, X130, X193, X214, X219, X273, X276, X321, and X362. In some embodiments, the specific amino acid residue differences as compared to SEQ ID NO: 2 at residue positions X108, X115, X116, X130, X193, X214, X219, X273, X276, X321, and X362, are selected from: X108L/Y, X115Q/W, X116S, X130T, X164T, X193A/D/E/V, X214G, X219A/D/L/V, X273A/E/T/V, X276A/T/L, X321A, and X362A/D/Q/S/V.

As will be appreciated by the skilled artisan, residue differences disclosed in Table 2 have no significant deleterious effects on pNB esterase activity and/or product selectivity for the engineered pNB esterase polypeptides, all of which maintain pNB esterase activity for the conversion of compound (2) to compound (1). Accordingly, the skilled artisan will understand that the residue differences at the residue positions disclosed herein can be used individually or in various combinations to produce engineered pNB esterase polypeptides having the desired functional properties, including, among others, pNB esterase activity, selectivity, and stability, in converting pNB-protected carbapenem compounds, such as compound (2) and its structural analogs, to its corresponding deprotected carbapenem compound, such as compound (1), imipenem.

In light of the guidance provided herein, it is further contemplated that any of the exemplary engineered polypeptides of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120 can be used as the starting amino acid sequence for synthesizing other engineered pNB esterase polypeptides, for example by subsequent rounds of evolution by adding new combinations of various amino acid differences from other polypeptides in Table 2, and other residue positions described herein. Further improvements may be generated by including amino acid differences at residue positions that had been maintained as unchanged throughout earlier rounds of evolution.

Accordingly, in some embodiments, the present disclosure provides engineered polypeptides having pNB esterase activity, and optionally improved properties in converting a pNB-protected substrate of compound (2) to a deprotected product compound (1) as compared to a reference polypeptide of SEQ ID NO:4, wherein the polypeptide comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO: 2 and one or more residue differences as compared to SEQ ID NO:2 at residue positions selected from X108. X115, X116, X130, X193, X214, X219, X273, X276, X321, and X362. In some embodiments, the specific amino acid residue differences as compared to SEQ ID NO: 2 at residue positions X108, X115, X116, X130, X193, X214, X219, X273, X276, X321, and X362, are selected from: X108L/Y, X115Q/W, X116S, X130T, X164T, X193A/D/E/V, X214G, X219A/D/L/V, X273A/E/T/V, X276A/T/L, X321A, and X362A/D/Q/S/V.

In some embodiments, the present disclosure provides an engineered polypeptide having pNB esterase activity that comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2 and one or more residue differences as compared to SEQ ID NO: 2 at residue positions selected from as compared to SEQ ID NO:2 at residue positions X108, X115, X193, X219. X273, X276, and X362 are selected from: X108L/Y, X115Q/W, X193A/D/E/V, X219A/D/L/V. X273A/E/T/V, X276A/T/L, and X362A/D/Q/S/V.

In some embodiments, the present disclosure provides an engineered polypeptide having pNB esterase activity comprises an amino acid sequence having at least 80% identity to a reference sequence of SEQ ID NO: 2 and one or more residue differences as compared to SEQ ID NO: 2 selected from: X108L/Y, X193A/D/E/V, X219A/D/L/V, X273A/E/T/V, and X362A/D/Q/S/V.

In some embodiments, the engineered polypeptide having pNB esterase activity comprises an amino acid sequence having at least 80% identity to a reference sequence of SEQ ID NO: 2 and a residue difference as compared to SEQ ID NO: 2 at position X193 selected from: X193A/D/E/V. In some embodiments, the amino acid residue difference as compared to SEQ ID NO: 2 at position X193 is X193V.

In some embodiments, the engineered polypeptide having pNB esterase activity of the present disclosure comprises an amino acid sequence having at least 80% identity to a reference sequence of SEQ ID NO: 2, and an amino acid difference as compared to SEQ ID NO: 2 of X193V, and further comprises residue differences as compared to SEQ ID NO: 2 at positions X219 and X273 selected from X219L/V and X273A/V. In some embodiments, the amino acid sequence further comprises residue differences as compared to SEQ ID NO: 2 at positions X108 and X362 selected from X108L/Y and X362A/D/Q/S/V. In still further embodiments, the engineered polypeptide further comprises a residue difference as compared to SEQ ID NO: 2 at position X115 selected from X115Q/W.

In some embodiments, the engineered polypeptide having pNB esterase activity of the present disclosure comprises an amino acid sequence having at least 80%, 85%, 86%, 87%, 88%, 89% 90%, 91%, 92%, 93%, 94%, 95%, 96%, 97%, 98%, 99% or more identity to a reference sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120, and one or more residue differences as compared to SEQ ID NO:2 at residue positions X108, X115, X116, X130, X193, X214, X219, X273, X276, X321, and X362. In some embodiments, the specific residue differences as compared to SEQ ID NO:2 at residue positions X108, X115, X116. X130, X193, X214, X219, X273. X276, X321, and X362 are selected from: X108L/Y, X115Q/W, X116S, X130T, X164T, X193A/D/E/V, X214G, X219A/D/L/V, X273A/E/T/V, X276A/T/L, X321A, and X362A/D/Q/S/V. In some embodiments, the reference sequence is selected from SEQ ID NO: 4, 12, 20, 36, 38, 54, 76, 80, 88, 112, and 116. In some embodiments, the reference sequence is SEQ ID NO:4. In some embodiments, the reference sequence is SEQ ID NO:12. In some embodiments, the reference sequence is SEQ ID NO:36. In some embodiments, the reference sequence is SEQ ID NO:38. In some embodiments, the reference sequence is SEQ ID NO:54. In some embodiments, the reference sequence is SEQ ID NO:76. In some embodiments, the reference sequence is SEQ ID NO:80. In some embodiments, the reference sequence is SEQ ID NO:88. In some embodiments, the reference sequence is SEQ ID NO:112. In some embodiments, the reference sequence is SEQ ID NO:116.

In some embodiments, the engineered polypeptide having pNB esterase activity of the present disclosure comprises an amino acid sequence having at least 80%, 85%, 86%, 87%, 88%, 89%, 90%, 91% 92%, 93%, 94%, 95%, 96%, 97%, 98%, 99% or more identity to a reference sequence selected from SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120, and a combination of residue differences as compared to SEQ ID NO: 2 selected from: (a) X193V, X219V, and X273A; (b) X108Y, X193D, X219V, X273A, and X362S; (c) X108Y, X193V, X219V, X273A, and X362Q; (d) X108Y, X115Q. X193V, X219L, X273A, and X362Q; and (e) X108Y, X115Q, X193V, X219V, X273A, and X362Q.

In some embodiments, the engineered polypeptides having pNB esterase activity disclosed above (and elsewhere herein) can have additional residue differences at other residue positions. In some embodiments, the engineered pNB esterases can have 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 additional residue differences as compared to SEQ ID NO:2. In some embodiments, the engineered pNB esterases can have 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 additional residue differences. In some embodiments, the amino acid sequence has additionally 1, 2, 3, 4, 5, 6, 7, 8, 9, 10, 11, 12, 13, 14, 15, 16, 18, 20, 21, 22, 23, 24, or 25 residue differences as compared to SEQ ID NO: 2.

In some embodiments, the engineered polypeptide having pNB esterase activity of the present disclosure comprises an amino acid sequence having at least 80% identity to a reference sequence of SEQ ID NO: 2, one or more amino acid residue difference as compared to SEQ ID NO: 2 selected from X108L/Y, X115Q/W, X193A/D/E/V, X219A/D/L/V, X273A/E/T/V, and X362A/D/Q/S/V, and the amino acid sequence further comprises one or more residue differences as compared to SEQ ID NO: 2 selected from: X116S, X130T, X164T, X214G, X276A/T/L, and X321A. In some embodiments, the amino acid sequence can further comprise a residue difference as compared to SEQ ID NO: 2 selected from: X49G, X94G, X96S, X227T, X251V, X267R. X271L, X274L, X313F, X322C/Y, X343V, X356R, X359A, X398L, X412E, X437T, X464A, and X481R.

The engineered pNB esterase polypeptide of SEQ ID NO:2 comprises the following seven amino acid differences as compared to the wild-type pNB esterase of *Bacillus subtilis* (GenBank Access. No.: AAA81915.1, GI:468046): I60V, L144M, P317S, H322R, L334S, M358V, and Y370F. Accordingly, in some embodiments, the present disclosure provides an engineered polypeptide having pNB-esterase activity comprises an amino acid sequence having at least 80% identity to SEQ ID NO: 2, and of any of the amino acid differences as compared to SEQ ID NO: 2 as disclosed herein (i.e., as disclosed in the exemplary polypeptides of SEQ ID NO: 4-120 of Table 2), but in which the amino acid sequence does not comprise a residue difference as compared to SEQ ID NO: 2 at a position selected from: X60, X144, X317, X322, X334, X358, and X370.

As will be appreciated by the skilled artisan, in some embodiments, one or a combination of residue differences above that is selected can be conserved in the engineered pNB esterases as a core sequence (or feature), and additional residue differences at other residue positions incorporated into the core sequence to generate additional engineered pNB esterase polypeptides with improved properties. Accordingly, it is to be understood for any engineered pNB esterase containing one or a subset of the residue differences above, the present disclosure contemplates other engineered pNB esterases that comprise the one or subset of the residue differences, and additionally one or more residue differences at the other residue positions disclosed herein. By way of example and not limitation, an engineered pNB esterase comprising a residue difference at residue position X193, can further incorporate one or more residue differences at the other residue positions, e.g., X108, X115, X116, X130, X214, X219. X273, X276, X321, and X362. Another example is an engineered pNB esterase comprising a residue difference at residue position X273, which can further comprise one or more residue differences at the other residue positions, e.g., X108, X115, X116, X130, X193, X214, X219, X276, X321, and X362. For each of the foregoing embodiments, the engineered pNB esterase can further comprise additional residue differences selected from: X108L/Y, X115Q/W, X116S, X130T, X164T, X193A/DE/V, X214G, X219A/D/L/V, X273A/E/T/V, X276A/T/L, X321A, and X362A/D/Q/S/V.

In some embodiments, the engineered pNB esterase polypeptide is capable of converting the substrate compound (2) to the product compound (1) with at least 1.2 fold, 1.5 fold, 2 fold, 3 fold, 4 fold, 5 fold, 10 fold, or more activity relative to the activity of the reference polypeptide of SEQ ID NO: 4. In some embodiments, the engineered pNB esterase polypeptide capable of converting the substrate compound (2) to the product compound (1) with at least 1.2 fold, 1.5 fold, 2 fold, 3 fold, 4 fold, 5 fold, 10 fold, or more activity relative to the activity of the reference polypeptide of SEQ ID NO:4 comprises an amino acid sequence having one or more residue differences as compared to SEQ ID NO:4 at a position selected from: X108, X115, X116, X130, X193. X214, X219, X273, X276, X321, and X362, wherein the specific residue difference is selected from: X108L/Y, X115Q/W, X116S, X130T, X164T, X193A/D/E/V, X214G, X219A/D/L/V, X273A/E/T/V, X276A/T/L, X321A, and X362A/D/Q/S/V. In some embodiments, the suitable reaction conditions are Reaction Conditions A as disclosed in Table 2. In some embodiments, the engineered pNB esterase polypeptide capable of converting the substrate compound (2) to the product compound (1) with at least 1.2 fold the activity relative to SEQ ID NO:4 comprises an amino acid sequence selected from: SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 78, 82, 84, 86, 88, 92, 94, 96, 98, 100, 102, 104, 106, 108, 110, 112, 114, 116, and 120.

In some embodiments, the engineered pNB esterase having pNB esterase activity comprises an amino acid sequence having at least 80% 85%, 86%, 87%, 88%, 89%, 90%, 91%, 92%, 93%, 94%, 95%, 96%, 97%, 98%, or 99% identity to one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120, and the amino acid residue differences as compared to SEQ ID NO:2 present in any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120, as provided in Table 2.

In addition to the residue positions specified above, any of the engineered pNB esterase polypeptides disclosed herein can further comprise other residue differences relative to SEQ ID NO:2 at other residue positions, i.e., residue positions other than X108, X115, X116, X130, X193, X214, X219, X273, X276, X321, and X362. Residue differences at these other residue positions provide for additional variations in the amino acid sequence without adversely affecting the ability of the polypeptide to carry out the pNB esterase reaction, such as the conversion of compound (2) to compound (1). Accordingly, in some embodiments, in addition to the amino acid residue differences of any one of the engineered pNB esterase polypeptides selected from SEQ ID NO: 4, 6, 8, 10, 12, 14, 16, 18, 20, 22, 24, 26, 28, 30, 32, 34, 36, 38.40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120, the sequence can further comprise 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, or 1-50 residue differences at other amino acid residue positions as compared to the SEQ ID NO: 2. In some embodiments, the number of amino acid residue differences as compared to the reference sequence can be 1, 2, 3, 4, 5, 6, 7, 8, 9, 10, 11, 12, 13, 14, 15, 16, 17, 18, 19, 20, 21, 22, 23, 24, 25, 30, 30, 35, 40, 45 or 50 residue positions. The residue difference at these other positions can include conservative changes or non-conservative changes. In some embodiments, the residue differences can comprise conservative substitutions and non-conservative substitutions as compared to the wild-type pNB esterase polypeptide of *B. subtilis* or the engineered pNB esterase polypeptide of SEQ ID NO: 2.

Amino acid residue differences at other positions relative to the wild-type pNB esterase of *B. subtilis* or the engineered polypeptide of SEQ ID NO: 2 and the effect of these differences on enzyme function are described for other engineered pNB esterase polypeptides in U.S. Pat. Nos. 5,906,930 and 5,945,325, each of which is incorporated by reference herein, and in the following publications, each of which is incorporated by reference herein: Moore et al., "Directed evolution of a para-nitrobenzyl esterase for aqueous-organic solvents," Nature Biotechnology 14: 458-467 (1996); Moore et al. "Strategies for the in vitro Evolution of Protein Function: Enzyme Evolution by Random Recombination of Improved Sequences," J. Mol. Biol. 272:336-347 (1997); Giver et al., "Directed evolution of a thermostable esterase," Proc. Natl. Acad. Sci. USA 95: 12809-12813 (October 1998). Accordingly, in some embodiments, one or more of the amino acid differences as compared to the sequence of SEQ ID NO: 2 can also be introduced into an engineered pNB esterase polypeptide of the present disclosure at residue positions selected from X49, X94, X96, X227. X251, X267, X271, X274, X313, X322, X343. X356, X359, X398, X412, X437, X464, and X481. In particular, the amino acid residues at the foregoing positions can be selected from the following: X49G, X94G, X96S, X227T, X251V, X267R, X271L, X274L, X313F, X322C/Y, X343V.

X356R, X359A, X398L, X412E, X437T, X464A, and X481R. Guidance on the choice of the amino acid residues at these residue positions and their effect on desirable enzyme properties can be found in the cited references.

In some embodiments, the present disclosure also provides engineered pNB esterase polypeptides that comprise a fragment of any of the engineered polypeptides described herein that retains the functional activity and/or improved property of that engineered pNB esterase. Accordingly, in some embodiments, the present disclosure provides a polypeptide fragment having pNB esterase activity, such as in converting compound (2) to compound (1) under suitable reaction conditions, wherein the fragment comprises at least about 80%, 90%, 95%, 96%, 97%, 98%, or 99% of a full-length amino acid sequence of an engineered pNB esterase polypeptide of the present disclosure, such as an exemplary engineered pNB esterase polypeptide selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120.

In some embodiments, the engineered pNB esterase polypeptide can have an amino acid sequence comprising a deletion of any one of the engineered pNB esterase polypeptides described herein, such as the exemplary engineered polypeptides of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120. Thus, for each and every embodiment of the engineered pNB esterase polypeptides of the disclosure, the amino acid sequence can comprise deletions of one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the pNB esterase polypeptides, where the associated functional activity and/or improved properties of the engineered pNB esterase described herein is maintained. In some embodiments, the deletions can comprise 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residues. In some embodiments, the number of deletions can be 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residues. In some embodiments, the deletions can comprise deletions of 1, 2, 3, 4, 5, 6, 7, 8, 9, 10, 11, 12, 13, 14, 15, 16, 18, 20, 21, 22, 23, 24, or 25 amino acid residues.

In some embodiments, the engineered pNB esterase polypeptide herein can have an amino acid sequence comprising an insertion as compared to any one of the engineered pNB esterase polypeptides described herein, such as the exemplary engineered polypeptides of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120. Thus, for each and every embodiment of the pNB esterase polypeptides of the disclosure, the insertions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, 20 or more amino acids, 30 or more amino acids, 40 or more amino acids, or 50 or more amino acids, where the associated functional activity and/or improved properties of the engineered pNB esterase described herein is maintained. The insertions can be to amino or carboxy terminus, or internal portions of the pNB esterase polypeptide.

In some embodiments, the engineered pNB esterase polypeptide herein can have an amino acid sequence comprising a sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120, and optionally one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions can be conservative or non-conservative substitutions.

In some embodiments, the present disclosure provides an engineered polypeptide having pNB esterase activity, which polypeptide comprises an amino acid sequence having at least 80%, 85%, 86%, 87%, 88%, 89%, 90%, 91%, 92%, 93%, 94%, 95%, 96%, 97%, 98%, or 99% identity to a sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120, with the proviso that the amino acid sequence is not identical to (that is, it excludes) any of the exemplary engineered pNB esterase polypeptide amino acid sequences disclosed in the following publications: U.S. Pat. No. 5,906,930; U.S. Pat. No. 5,945,325; Moore et al., "Directed evolution of a para-nitrobenzyl esterase for aqueous-organic solvents," Nature Biotechnology 14: 458-467 (1996); Moore et al. "Strategies for the in vitro Evolution of Protein Function: Enzyme Evolution by Random Recombination of Improved Sequences," *J. Mol. Biol.* 272:336-347 (1997); and Giver et al., "Directed evolution of a thermostable esterase," *Proc. Natl. Acad. Sci. USA* 95: 12809-12813 (October 1998).

In the above embodiments, the suitable reaction conditions for the engineered polypeptides can be those described in Table 2, the Examples, and elsewhere herein.

In some embodiments, the engineered polypeptides of the disclosure can be in the form of fusion polypeptides in which the engineered polypeptides are fused to other polypeptides, such as, by way of example and not limitation, antibody tags (e.g., myc epitope), purification sequences (e.g., His tags for binding to metals), and cell localization signals (e.g., secretion signals). Thus, the engineered polypeptides described herein can be used with or without fusions to other polypeptides.

It is to be understood that the engineered polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereoisomers of the genetically-encoded amino acids; 2,3-diaminopropionic acid (Dpr); α-aminoisobutyric acid (Aib): ϵ-aminohexanoic acid (Aha); δ-aminovaleric acid (Ava); N-methylglycine or sarcosine (MeGly or Sar): ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf): 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1 nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen): 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisoleucine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L- or D-configuration.

Those of skill in the art will recognize that amino acids or residues bearing side chain protecting groups may also comprise the engineered polypeptides described herein. Non-limiting examples of such protected amino acids, which in this case belong to the aromatic category, include (protecting groups listed in parentheses), but are not limited to: Arg (tos), Cys (methylbenzyl), Cys (nitropyridinesulfenyl), Glu (δ-benzylester), Gln (xanthyl), Asn (N-δ-xanthyl), His (bom), His (benzyl), His (tos), Lys (fmoc), Lys (tos), Ser (O-benzyl), Thr (O-benzyl) and Tyr (O-benzyl).

Non-encoding amino acids that are conformationally constrained of which the engineered polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

In some embodiments, the engineered pNB esterase polypeptides can be provided on a solid support, such as a membrane, resin, solid carrier, or other solid phase material. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a solid support can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location.

In some embodiments, the engineered polypeptides having pNB esterase activity of the present disclosure can be immobilized on a solid support such that they retain their improved activity, and/or other improved properties relative to the reference polypeptide of SEQ ID NO: 4. In such embodiments, the immobilized engineered pNB esterase polypeptides can facilitate the biocatalytic conversion of pNB-protected substrate of compound (2), or other structurally analogous pNB-protected substrate compounds, to the deprotected product compound (1), imipenem, or a corresponding structural analog product carbapenem, and after the reaction is complete are easily retained (e.g., by retaining beads on which polypeptide is immobilized) and then reused or recycled in subsequent reactions. Such immobilized enzyme processes allow for further efficiency and cost reduction. Accordingly, it is further contemplated that any of the methods of using the engineered pNB esterase polypeptides of the present disclosure can be carried out using the same engineered pNB esterase polypeptides bound or immobilized on a solid support.

Methods of enzyme immobilization are well-known in the art. The engineered pNB esterase polypeptide can be bound non-covalently or covalently. Various general methods for conjugation and immobilization of enzymes to solid supports (e.g., resins, membranes, beads, glass, etc.) are well known in the art and described in e.g.; Yi et al., "Covalent immobilization of co-transaminase from *Vibrio fluvialis* JS17 on chitosan beads," *Process Biochemistry* 42(5): 895-898 (May 2007); Martin et al., "Characterization of free and immobilized (S)-aminotransferase for acetophenone production," *Applied Microbiology and Biotechnology* 76(4): 843-851 (September 2007); Koszelewski et al., "Immobilization of ω-transaminases by encapsulation in a sol-gel/celite matrix," *Journal of Molecular Catalysis B: Enzymatic,* 63: 39-44 (April 2010); Truppo et al., "Development of an Improved Immobilized CAL-B for the Enzymatic Resolution of a Key Intermediate to Odanacatib," *Organic Process Research & Development*, published online: dx.doi.org/10.1021/op$^{200}$157c; Hermanson, G. T., Bioconjugate Techniques, Second Edition, Academic Press (2008); Mateo et al., "Epoxy sepabeads: a novel epoxy support for stabilization of industrial enzymes via very intense multipoint covalent attachment," *Biotechnology Progress* 18(3):629-34 (2002); and Bioconjugation Protocols: Strategies and Methods, In Methods in Molecular Biology, C. M. Niemeyer ed., Humana Press (2004); the disclosures of each which are incorporated by reference herein.

Solid supports useful for immobilizing the engineered pNB esterases of the present disclosure include but are not limited to beads or resins comprising polymethacrylate with epoxide functional groups, polymethacrylate with amino epoxide functional groups, styrene/DVB copolymer or polymethacrylate with octadecyl functional groups. Exemplary solid supports useful for immobilizing the engineered pNB esterases of the present disclosure include, but are not limited to, chitosan beads. Eupergit C, and SEPABEADs (Mitsubishi), including the following different types of SEPABEAD: EC-EP, EC-HFA/S, EXA252, EXE119 and EXE120.

In some embodiments, the engineered polypeptides can be in various forms, for example, such as an isolated preparation, as a substantially purified enzyme, whole cells transformed with gene(s) encoding the enzyme, and/or as cell extracts and/or lysates of such cells. The enzymes can be lyophilized, spray-dried, precipitated or be in the form of a crude paste, as further discussed below.

In some embodiments, the engineered polypeptide described herein can be provided in the form of kits. The enzymes in the kits may be present individually or as a plurality of enzymes. The kits can further include reagents for carrying out the enzymatic reactions, substrates for assessing the activity of enzymes, as well as reagents for detecting the products. The kits can also include reagent dispensers and instructions for use of the kits.

In some embodiments, the engineered polypeptides can be provided on the solid support in the form of an array in which the polypeptides are arranged in positionally distinct locations. The array can be used to test a variety of substrate compounds for conversion by the polypeptides. A plurality of supports can be configured on an array at various locations, addressable for robotic delivery of reagents, or by detection methods and/or instruments. Various methods for conjugation to substrates, e.g., membranes, beads, glass, etc. are described in, among others, Hermanson, G. T., Bioconjugate Techniques, 2nd Edition, Academic Press; (2008), and Bioconjugation Protocols: Strategies and Methods, In Methods in Molecular Biology, C. M. Niemeyer ed., Humana Press (2004); the disclosures of which are incorporated herein by reference. In some embodiments, the kits of the present disclosure include arrays comprising a plurality of different engineered polypeptides disclosed herein at different addressable position, wherein the different polypeptides are different variants of a reference sequence each having at least one different improved enzyme property. Such arrays comprising a plurality of engineered polypeptides and methods of their use are described in e.g., WO2009008908.

5.4 polynucleotides encoding engineered polypeptides, expression vectors and Host cells In another aspect, the present disclosure provides polynucleotides encoding the engineered pNB esterase polypeptides described herein. The polynucleotides may be operatively linked to one or more heterologous regulatory sequences that control gene expression to create a recombinant polynucleotide capable of expressing the polypeptide. Expression constructs containing a heterologous polynucleotide encoding the engineered pNB esterase can be introduced into appropriate host cells to express the corresponding pNB esterase polypeptide.

As will be apparent to the skilled artisan, availability of a protein sequence and the knowledge of the codons corresponding to the various amino acids provide a description of all the polynucleotides capable of encoding the subject polypeptides. The degeneracy of the genetic code, where the same amino acids are encoded by alternative or synonymous codons, allows an extremely large number of nucleic acids to be made, all of which encode the improved pNB esterase enzymes. Thus, having knowledge of a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made encoding the polypeptides described herein by selecting combinations based on the possible codon choices, and all such variations are to be considered specifically disclosed for any polypeptide described herein, including the amino acid sequences presented in Table 2, and disclosed in the Sequence Listing incorporated by reference herein as SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120.

In various embodiments, the codons are preferably selected to fit the host cell in which the protein is being produced. For example, preferred codons used in bacteria are used for expression in bacteria; preferred codons used in yeast are used for expression in yeast; and preferred codons used in mammals are used for expression in mammalian cells. In some embodiments, all codons need not be replaced to optimize the codon usage of the pNB esterases since the natural sequence will comprise preferred codons and because use of preferred codons may not be required for all amino acid residues. Consequently, codon optimized polynucleotides encoding the pNB esterase enzymes may contain preferred codons at about 40%, 50%, 60%, 70%, 80%, or greater than 90%/o of codon positions of the full length coding region.

In some embodiments, as described above, the polynucleotide encodes an engineered polypeptide having pNB esterase activity with the properties disclosed herein, such as the ability to convert the substrate compound (2) to the product compound (1), where the polypeptide comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120, and one or more residue differences as compared to the reference polypeptide of SEQ ID NO:2 at residue positions X108, X115, X16, X130, X193, X214, X219, X273, X276. X321, and X362. In some embodiments, the specific residue differences as compared to SEQ ID NO:2 at residue positions X108. X115, X116, X130, X193, X214, X219, X273. X276, X321, and X362 are selected from: X108L/Y, X115Q/W, X116S, X130T, X164T, X193A/D/E/V, X214G, X219A/D/L/V, X273A/E/T/V, X276A/T/L, X321A, and X362A/D/Q/S/V. In some embodiments, the reference sequence is selected from SEQ ID NO: 4, 12, 20, 36, 38, 54, 76, 80, 88, 112, and 116. In some embodiments, the reference sequence is SEQ ID NO:4. In some embodiments, the reference sequence is SEQ ID NO: 12. In some embodiments, the reference sequence is SEQ ID NO:36. In some embodiments, the reference sequence is SEQ ID NO:38. In some embodiments, the reference sequence is SEQ ID NO:54. In some embodiments, the reference sequence is SEQ ID NO:76. In some embodiments, the reference sequence is SEQ ID NO:80. In some embodiments, the reference sequence is SEQ ID NO:88. In some embodiments, the reference sequence is SEQ ID NO:112. In some embodiments, the reference sequence is SEQ ID NO:116.

In some embodiments, the polynucleotide encodes an engineered polypeptide having pNB esterase activity with the properties disclosed herein, wherein the polypeptide comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2 and one or more residue differences as compared to SEQ ID NO: 2 at residue positions selected from as compared to SEQ ID NO:2 at residue positions X108, X115, X193, X219, X273, X276, and X362 are selected from: X108L/Y, X115Q/W, X193A/D/E/V, X219A/D/L/V, X273A/E/T/V, X276A/T/L, and X362A/D/Q/S/V.

In some embodiments, the polynucleotide encodes an engineered polypeptide having pNB esterase activity, wherein the polypeptide comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2 and at least a combination of residue differences as compared to SEQ ID NO: 2 selected from: (a) X193V, X219V, and X273A (b) X108Y, X193D, X219V, X273A, and X362S; (c) X108Y, X193V, X219V, X273A, and X362Q; (d) X108Y, X115Q, X193V, X219L, X273A, and X362Q; and (e) X108Y, X115Q, X193V, X219V, X273A, and X362Q.

In some embodiments, the polynucleotide encodes an engineered polypeptide having pNB esterase activity, wherein the polypeptide comprises an amino acid sequence having at least 80%, 85%, 86%, 87%, 88%, 89%, 900%, 91%, 92%, 93%, 94%, 95%, 96%, 97%, 98%, or 99% identity to a reference polypeptide selected from any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120, with the proviso that the amino acid sequence comprises any one of the set of residue differences as compared to SEQ ID NO: 2 contained in any one of the polypeptide sequences of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120, as listed in Table 2.

In some embodiments, the polynucleotide encoding the engineered pNB esterase comprises a polynucleotide sequence selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, and 119.

In some embodiments, the polynucleotides are capable of hybridizing under highly stringent conditions to a reference polynucleotide sequence selected from SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, and 119, or a complement thereof, and encodes a polypeptide having pNB esterase activity with one or more of the improved properties described herein. In some embodiments, the polynucleotide capable of hybridizing under highly stringent conditions encodes a pNB esterase polypeptide comprising an amino acid sequence that has one or more residue differences as compared to SEQ ID NO: 2 at residue positions selected from X108, X115, X116, X130, X193, X214, X219, X273, X276. X321, and X362, and optionally wherein the specific residue differences as compared to SEQ ID NO:2 are selected from: X108L/Y, X115Q/W, X116S, X130T, X164T, X193A/D/E/V, X214G, X219A/D/L/V, X273A/E/T/V, X276A/T/L, X321A, and X362A/D/Q/S/V.

In some embodiments, the polynucleotides encode the polypeptides described herein but have about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered pNB esterase. In some embodiments, the reference polynucleotide sequence is selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, and 119.

An isolated polynucleotide encoding any of the engineered pNB esterase polypeptides herein may be manipulated in a variety of ways to provide for expression of the polypeptide. In some embodiments, the polynucleotides encoding the polypeptides can be provided as expression vectors where one or more control sequences is present to regulate the expression of the polynucleotides and/or polypeptides. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in e.g., Sambrook et al. 2001, "Molecular Cloning: A Laboratory Manual," 3rd Ed., Cold Spring Harbor Laboratory Press; and Current Protocols in Molecular Biology, Ausubel. F. ed., Greene Pub. Associates, 1998, and updates to 2006.

In some embodiments, the control sequences include among others, promoter, leader sequence, polyadenylation sequence, propeptide sequence, signal peptide sequence, and transcription terminator. Suitable promoters can be selected based on the host cells used. For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus* lichenformis alpha-amylase gene (amyL), *Bacillus stearothermophilus* maltogenic amylase gene (amyM), *Bacillus* amvloliquefaciens alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proc. Natl Acad. Sci. USA 75: 3727-3731), as well as the tac promoter (DeBoer et al., 1983, Proc. Natl Acad. Sci. USA 80: 21-25). Exemplary promoters for filamentous fungal host cells, include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus* or zae alkaline protease, *Aspergillus* orvzae triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. Exemplary yeast cell promoters can be from the genes can be from the genes for *Saccharomvces cerevisiae enolase* (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992. Yeast 8:423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention. For example, exemplary transcription terminators for filamentous fungal host cells can be obtained from the genes for *Aspergillus orvzae* TAKA amylase, *Aspergillus niger* glucoamylase. *Aspergillus nidulans* anthranilate synthase, *Aspergillus niger* alpha-glucosidase, and *Fusarium oxysporum* trypsin-like protease. Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus orvzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995, Mol Cell Bio 15:5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. Any signal peptide coding region which directs the expressed polypeptide into the secretory pathway of a host cell of choice may be used for expression of the engineered polypeptides. Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase. *Bacillus stearothermophilus* neutral proteases (nprT, nprS, nprM), and *Bacillus subtilis* prsA. Further signal peptides are described by Simonen and Palva, 1993, Microbiol Rev 57:109-137. Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase. *Humicola insolens* cellulase, and *Humicola lanuginosa* lipase. Useful signal peptides for yeast host cells can be from the genes for *Saccharomyces cerevisiae* alpha-factor and *Saccharomyces cerevisiae* invertase.

The control sequence may also be a propeptide coding region that codes for an amino acid sequence positioned at the amino terminus of a polypeptide. The resultant polypeptide is referred to as a proenzyme or propolypeptide (or a zymogen in some cases). A propolypeptide can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836). Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

In another aspect, the present disclosure is also directed to a recombinant expression vector comprising a polynucleotide encoding an engineered pNB esterase polypeptide, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferases), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus.*

In another aspect, the present disclosure provides a host cell comprising a polynucleotide encoding an engineered pNB esterase polypeptide of the present disclosure, the polynucleotide being operatively linked to one or more control sequences for expression of the pNB esterase enzyme in the host cell. Host cells for use in expressing the polypeptides encoded by the expression vectors of the present invention are well known in the art and include but are not limited to, bacterial cells, such as *E. coli, Vibrio fluvialis, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9) cells; animal cells such as CHO, COS, BHK, 293, and Bowes melanoma cells; and plant cells. An exemplary host cells are *Escherichia coli* W3110 (ΔfhuA) and BL21.

Accordingly, in another aspect, the present disclosure provides methods of manufacturing the engineered pNB esterase polypeptides, where the method can comprise culturing a host cell capable of expressing a polynucleotide encoding the engineered pNB esterase polypeptide under conditions suitable for expression of the polypeptide. The method can further comprise isolated or purifying the expressed pNB esterases polypeptide, as described herein.

Appropriate culture mediums and growth conditions for the above-described host cells are well known in the art. Polynucleotides for expression of the pNB esterase may be introduced into cells by various methods known in the art. Techniques include, among others, electroporation, biolistic particle bombardment, liposome mediated transfection, calcium chloride transfection, and protoplast fusion.

For the embodiments herein, the engineered polypeptides and corresponding polynucleotides can be obtained using methods used by those skilled in the art. The parental polynucleotide sequence encoding the wild-type pNB esterase polypeptide of *Bacillus subtilis* is disclosed in Zock et al., "The *Bacillus subtilis* pnbA gene encoding p-nitrobenzyl esterase: cloning, sequence and high-level expression in *Escherichia coli," Gene* 151: 37-43 (1994), and U.S. Pat. No. 5,468,632, and methods of generating engineered pNB esterase polypeptides with improved stability are disclosed in U.S. Pat. Nos. 5,906,930 and 5,945,325, each of which is incorporated by reference herein, and in the following publications, each of which is incorporated by reference herein: Moore et al., "Directed evolution of a para-nitrobenzyl esterase for aqueous-organic solvents," *Nature Biotechnology* 14: 458-467 (1996); Moore et al. "Strategies for the in vitro Evolution of Protein Function: Enzyme Evolution by Random Recombination of Improved Sequences," *J. Mol. Biol.* 272:336-347 (1997); Giver et al., "Directed evolution of a thermostable esterase," *Proc. Natl. Acad. Sci. USA* 95: 12809-12813 (October 1998).

The engineered pNB esterases with the properties disclosed herein can be obtained by subjecting the polynucleotide encoding the naturally occurring or engineered pNB esterase to mutagenesis and/or directed evolution methods known in the art, and as described herein. An exemplary directed evolution technique is mutagenesis and/or DNA shuffling as described in Stemmer, 1994, Proc. Natl. Acad. Sci. USA 91:10747-10751; WO 95/22625; WO 97/0078; WO 97/35966; WO 98/27230; WO 00/42651; WO 01/75767 and U.S. Pat. No. 6,537,746. Other directed evolution procedures that can be used include, among others, staggered extension process (StEP), in vitro recombination (Zhao et al., 1998, Nat. Biotechnol. 16:258-261), mutagenic PCR (Caldwell et al., 1994, PCR Methods Appl. 3:S136-S140), and cassette mutagenesis (Black et al., 1996, Proc NatI Acad Sci USA 93:3525-3529). Mutagenesis and directed evolution techniques useful for the purposes herein are also described in the following references: Ling, et al., 1997, Anal. Biochem. 254(2):157-78; Dale et al., 1996, "Oligonucleotide-directed random mutagenesis using the phosphorothioate method," In Methods Mol. Biol. 57:369-74; Smith. 1985, Ann. Rev. Genet. 19:423-462; Botstein et al., 1985, Science 229:1193-1201; Carter, 1986. Biochem. J. 237:1-7; Kramer et al., 1984, Cell, 38:879-887; Wells et al., 1985. Gene 34:315-323; Minshull et al., 1999, Curr Opin Chem Biol 3:284-290; Christians et al., 1999, Nature Biotech 17:259-264; Crameri et al., 1998, Nature 391:288-291; Crameri et al., 1997, Nature Biotech 15:436-438; Zhang et al., 1997, Proc Natl Acad Sci USA 94:45-4-4509; Crameri et al., 1996, Nature Biotech 14:315-319; Stemmer, 1994, Nature 370:389-391; Stemmer, 1994. Proc Natl Acad Sci USA 91:10747-10751; WO 95/22625; WO 97/0078; WO 97/35966; WO 98/27230; WO 00/42651; WO 01/75767 and U.S. Pat. No. 6,537,746. All publications are incorporated herein by reference.

The clones obtained following mutagenesis treatment can be screened for engineered pNB esterases having a desired improved enzyme property. For example, where the improved enzyme property desired is thermostability, enzyme activity may be measured after subjecting the enzyme preparations to a defined temperature and measuring the amount of enzyme activity remaining after heat treatments. Clones containing a polynucleotide encoding a pNB esterase are then isolated, sequenced to identify the nucleotide sequence changes (if any), and used to express the enzyme in a host cell. Measuring enzyme activity from the expression libraries can be performed using the standard biochemistry techniques, such as HPLC analysis.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides disclosed herein can be prepared by chemical synthesis using, e.g., the classical phosphoramidite method described by Beaucage et al., 1981. Tet Lett 22:1859-69, or the method described by Matthes et al., 1984. EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors.

Accordingly, in some embodiments, a method for preparing the engineered pNB esterase polypeptide can comprise: (a) synthesizing a polynucleotide encoding a polypeptide comprising an amino acid sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92.94, 96, 98, 100, 102, 104, 106, 108, 110, 112, 114, 116, 118, and 120 and having one or more residue differences as compared to SEQ ID NO: 2 at residue positions selected from: X108, X115, X116, X130, X193, X214, X219, X273, X276, X321, and X362, and wherein the specific residue differences as compared to SEQ ID NO:2 optionally are selected from: X108L/Y, X115Q/W, X116S, X130T, X164T, X193A/D/E/V, X214G, X219A/D/L/V, X273A/E/T/V, X276A/T/L, X321A, and X362A/D/Q/S/V; and (b) expressing the pNB esterase polypeptide encoded by the polynucleotide.

In some embodiments of the method, the amino acid sequence encoded by the polynucleotide can optionally have one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions can be conservative or non-conservative substitutions.

The expressed engineered pNB esterase can be measured for the desired improved property, e.g., activity, selectivity, stability, and/or product tolerance, in the conversion of compound (2) to compound (1) by any of the assay conditions described herein.

In some embodiments, any of the engineered pNB esterase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are provided in Table 2 and the Examples, and also commercially available, e.g., CelLytic B™ from Sigma-Aldrich of St. Louis Mo.

Chromatographic techniques for isolation of the pNB esterase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved pNB esterase enzymes. For affinity chromatography purification, any antibody which specifically binds the pNB esterase polypeptide may be used. For the production of antibodies, various host animals, including but not limited to rabbits, mice, rats, etc., may be immunized by injection with a pNB esterase polypeptide, or a fragment thereof. The pNB esterase polypeptide or fragment may be attached to a suitable carrier, such as BSA, by means of a side chain functional group or linkers attached to a side chain functional group.

5.7 Methods of Using the Engineered pNB Esterase Polypeptides

As noted above, the engineered pNB esterase polypeptides of the present disclosure were evolved to efficiently convert the pNB-protected substrate of compound (2) to the corresponding product compound (1), imipenem, under suitable reaction conditions. The structural features of the engineered pNB esterase polypeptides allow for the conversion of the pNB-protected substrate of compound (2) to their corresponding deprotected product of compound (1), imipenem. Accordingly, in another aspect the present disclosure provides a process for preparing carbapenem antibiotic of compound (1), imipenem, or a salt or hydrate of compound (1),

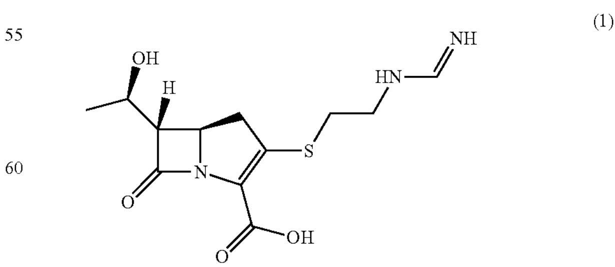

(1)

wherein the method comprises contacting a substrate compound (2), or a salt or hydrate of compound (2), (2)

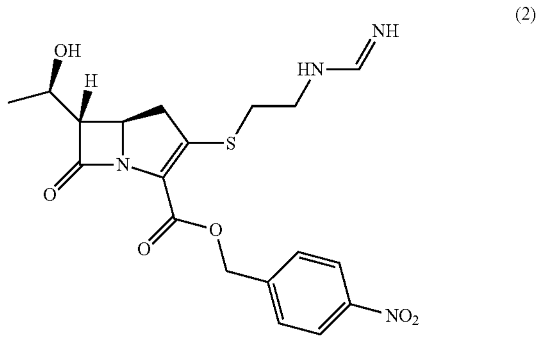 [SMILES: C[C@@H](O)[C@H]1C(=O)N2C(C(=O)OCc3ccc([N+](=O)[O-])cc3)=C(SCCNC=N)C[C@H]12]

with an engineered pNB esterase polypeptide of the present disclosure under suitable reaction conditions.

The structural features of the engineered pNB esterase polypeptides can also provide engineered pNB esterases capable of converting of other pNB-protected carbapenem substrates that are structural analogs of compound (2). Accordingly, in another aspect, the present disclosure provides processes using the engineered pNB esterase polypeptides to carry out a deprotection reaction in which a pNB group is removed from a pNB-protected carbapenem compound. Generally, the process for performing the biocatalytic pNB deprotection reaction comprises contacting or incubating an engineered pNB esterase polypeptide of the disclosure with the pNB-protected compound with under reaction conditions suitable for deprotecting the carbapenem precursor and yielding the desired carbapenem compound.

For the foregoing processes, any of the engineered pNB esterase polypeptides described herein can be used. By way of example and without limitation, in some embodiments, the process can use an engineered polypeptide having pNB esterase activity of the present disclosure comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120, and one or more residue differences as compared to SEQ ID NO:2 at residue positions selected from X108, X115, X116, X130, X193, X214, X219, X273, X276, X321, and X362. In some embodiments, the specific residue differences as compared to SEQ ID NO:2 at residue positions X108, X115, X116, X130, X193, X214, X219, X273, X276, X321, and X362 are selected from: X108L/Y, X115Q/W, X116S, X130T, X164T, X193A/D/E/V, X214G, X219A/D/V, X273A/E/T/V, X276A/T/L, X321A, and X362A/D/Q/S/V. In some embodiments, the reference sequence is selected from SEQ ID NO: 4, 12, 20, 36, 38, 54, 76, 80, 88, 112, and 116. In some embodiments, the reference sequence is SEQ ID NO:4. In some embodiments, the reference sequence is SEQ ID NO:12. In some embodiments, the reference sequence is SEQ ID NO:36. In some embodiments, the reference sequence is SEQ ID NO:38. In some embodiments, the reference sequence is SEQ ID NO:54. In some embodiments, the reference sequence is SEQ ID NO:76. In some embodiments, the reference sequence is SEQ ID NO:80. In some embodiments, the reference sequence is SEQ ID NO:88. In some embodiments, the reference sequence is SEQ ID NO:112. In some embodiments, the reference sequence is SEQ ID NO:116.

In some embodiments, exemplary pNB esterase polypeptides capable of carrying out the processes herein can be a polypeptide comprising an amino acid sequence selected from SEQ ID NO: 4, 6, 8, 10, 12, 14, 16, 18, 20, 22, 24, 26, 28, 30, 32, 34, 36, 38.40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120. Guidance on the choice and use of the engineered pNB esterase polypeptides is provided in the descriptions herein, for example Table 2 and the Examples.

In the embodiments herein and illustrated in the Examples, various ranges of suitable reaction conditions that can be used, including but not limited, to ranges of pH, temperature, buffer, solvent system, substrate loading, polypeptide loading, pressure, and reaction time. Further suitable reaction conditions for carrying out the process for biocatalytic conversion of substrate compounds to product compounds using an engineered pNB esterase polypeptide described herein can be readily optimized in view of the guidance provided herein by routine experimentation that includes, but is not limited to, contacting the engineered pNB esterase polypeptide and substrate compound under experimental reaction conditions of concentration, pH, temperature, solvent conditions, and detecting the product compound.

Substrate compound in the reaction mixtures can be varied, taking into consideration, for example, the desired amount of product compound, the effect of substrate concentration on enzyme activity, stability of enzyme under reaction conditions, and the percent conversion of substrate to product. In some embodiments, the suitable reaction conditions comprise a substrate compound loading of at least about 0.5 to about 200 g/L, 1 to about 200 g/L, about 5 to about 150 g/L, about 10 to about 100 g/L, about 20 to about 100 g/L, or about 50 to about 100 g/L. In some embodiments, the suitable reaction conditions comprise a substrate compound loading of at least about 0.5 g/L, at least about 1 g/L, at least about 5 g/L, at least about 10 g/L, at least about 15 g/L, at least about 20 g/L, at least about 30 g/L, at least about 50 g/L, at least about 75 g/L, at least about 100 g/L, at least about 150 g/L or at least about 200 g/L, or even greater. The values for substrate loadings provided herein are based on the molecular weight of compound (2), however it also contemplated that the equivalent molar amounts of various hydrates and salts of compound (2) also can be used in the process. In addition, structural analogs of the substrate of compound (2), can also be used in appropriate amounts, in light of the amounts used for the substrate of compound (2).

In carrying out the reactions described herein, the engineered pNB esterase polypeptide may be added to the reaction mixture in the form of a purified enzyme, whole cells transformed with gene(s) encoding the enzyme, and/or as cell extracts and/or lysates of such cells. Whole cells transformed with gene(s) encoding the engineered pNB esterase enzyme or cell extracts, lysates thereof, and isolated enzymes may be employed in a variety of different forms, including solid (e.g., lyophilized, spray-dried, and the like) or semisolid (e.g., a crude paste). The cell extracts or cell lysates may be partially purified by precipitation (ammonium sulfate, polyethyleneimine, heat treatment or the like), followed by a desalting procedure prior to lyophilization (e.g., ultrafiltration, dialysis, and the like). Any of the cell preparations may be stabilized by crosslinking using known crosslinking agents, such as, for example, glutaraldehyde, or immobilization to a solid phase (e.g., Eupergit C, and the like).

The gene(s) encoding the engineered pNB esterase polypeptides can be transformed into host cell separately or together into the same host cell. For example, in some embodiments one set of host cells can be transformed with gene(s) encoding one engineered pNB esterase polypeptide and another set can be transformed with gene(s) encoding another engineered pNB esterase polypeptide. Both sets of transformed cells can be utilized together in the reaction mixture in the form of whole cells, or in the form of lysates or extracts derived therefrom. In other embodiments, a host cell can be transformed with gene(s) encoding multiple engineered pNB esterase polypeptides. In some embodiments the engineered polypeptides can be expressed in the form of secreted polypeptides and the culture medium containing the secreted polypeptides can be used for the pNB esterase reaction.

The enhancements in activity and/or product selectivity of the engineered pNB esterase polypeptides disclosed herein provide for processes wherein higher percentage conversion can be achieved with lower concentrations of the engineered polypeptide. In some embodiments of the process, the suitable reaction conditions comprise an engineered polypeptide concentration of about 0.01 to about 50 g/L; about 0.05 to about 50 g/L; about 0.1 to about 40 g/L; about 1 to about 40 g/L; about 2 to about 40 g/L: about 5 to about 40 g/L; about 5 to about 30 g/L: about 0.1 to about 10 g/L; about 0.5 to about 10 g/L; about 1 to about 10 g/L; about 0.1 to about 5 g/L; about 0.5 to about 5 g/L; or about 0.1 to about 2 g/L. In some embodiments, the pNB esterase polypeptide is concentration at about 0.01, 0.05, 0.1, 0.2, 0.5, 1, 2, 5, 10, 15, 20, 25, 30, 35, 40, or 50 g/L.

During the course of the pNB esterase reactions, the pH of the reaction mixture may change. The pH of the reaction mixture may be maintained at a desired pH or within a desired pH range. This may be done by adding an acid or base, before and/or during the course of the reaction. Alternatively, the pH may be controlled by using a buffer. Accordingly, in some embodiments, the reaction condition comprises a buffer. Suitable buffers to maintain desired pH ranges are known in the art and include, by way of example and not limitation, phosphate, 2-(N-morpholino)ethanesulfonic acid (MES), borate, carbonate, triethanolamine (TEA), and the like. In some embodiments, the buffer is borate. In some embodiments of the process, the suitable reaction conditions comprise a buffer solution of MES, where the MES concentration is from about 0.01 to about 0.4 M, 0.05 to about 0.4 M, 0.1 to about 0.3 M, or about 0.1 to about 0.2 M. In some embodiments, the reaction condition comprises a MES concentration of about 0.01, 0.02, 0.03, 0.04, 0.05, 0.07, 0.1, 0.12, 0.14, 0.16, 0.18, 0.2, 0.3, or 0.4 M. In some embodiments, the reaction conditions comprise water as a suitable solvent with no buffer present.

In the embodiments of the process, the reaction conditions can comprise a suitable pH. The desired pH or desired pH range can be maintained by use of an acid or base, an appropriate buffer, or a combination of buffering and acid or base addition. The pH of the reaction mixture can be controlled before and/or during the course of the reaction. In some embodiments, the suitable reaction conditions comprise a solution pH from about 5 to about 12, pH from about 6 to about 9, pH from about 6 to about 8, pH from about 6.5 to about 7.5, or pH from about 7 to about 8. In some embodiments, the reaction conditions comprise a solution pH of about 6, 6.5, 7, 7.5, 8, 8.5, 9, 9.5, 10, 10.5, 11, 11.5 or 12.

In the embodiments of the processes herein, a suitable temperature can be used for the reaction conditions, for example, taking into consideration the increased reaction rate at higher temperatures, and the activity of the enzyme during the reaction time period. For example, the engineered polypeptides of the present disclosure have increased stability relative to naturally occurring pNB esterase polypeptide e.g., the wild-type polypeptide of SEQ ID NO: 2, which allow the engineered polypeptides to be used at higher temperatures for increased conversion rates and improved substrate solubility characteristics. Accordingly, in some embodiments, the suitable reaction conditions comprise a temperature of about 5° C. to about 65° C., about 10° C. to about 60° C., about 15° C. to about 55° C., about 15° C. to about 45° C., about 15° C. to about 35° C. about 20° C. to about 55° C., or about 30° C. to about 60° C. In some embodiments, the suitable reaction conditions comprise a temperature of about 5° C., about 10° C., about 15° C., about 20° C., about 25° C., about 30° C., about 35° C., about 40° C., about 45° C., about 50° C., about 55° C., about 60° C., about 65° C., or about 70° C.

In some embodiments, higher temperatures (e.g., above 25° C.) can result in increased undesirable side-products, such as the β-lactam ring-opened diacid imipenem side-product of compound (3). Accordingly, in some embodiments, the suitable reaction conditions comprise a temperature of about 5° C. to about 30° C., about 10° C. to about 25° C., about 10° C. to about 20° C., or about 15° C. to about 20° C. In some embodiments, the suitable reaction conditions comprise a temperature of about 5° C., about 10° C., about 15° C., about 20° C. about 25° C. or about 30° C.

In some embodiments, the temperature during the enzymatic reaction can be maintained at a temperature throughout the course of the reaction or adjusted over a temperature profile during the course of the reaction.

The processes herein are generally carried out in a solvent. Suitable solvents include water, aqueous buffer solutions, organic solvents, polymeric solvents, and/or co-solvent systems, which generally comprise aqueous solvents, organic solvents and/or polymeric solvents. The aqueous solvent (water or aqueous co-solvent system) may be pH-buffered or unbuffered. In some embodiments, the processes are generally carried out in an aqueous co-solvent system comprising an organic solvent (e.g., ethanol, isopropanol (IPA), dimethylformamide (DMF), dimethyl sulfoxide (DMSO), ethyl acetate, butyl acetate, I-octanol, heptane, octane, methyl t-butyl ether (MTBE), toluene, and the like), ionic or polar solvents (e.g., 1 ethyl 4 methylimidazolium tetrafluoroborate, 1 butyl 3 methylimidazolium tetrafluoroborate, 1 butyl 3 methylimidazolium hexafluorophosphate, glycerol, polyethylene glycol, and the like). In general, the co-solvent component of an aqueous co-solvent system is chosen such that it does not adversely inactivate the pNB esterase enzyme under the reaction conditions. Appropriate co-solvent systems can be readily identified by measuring the enzymatic activity of the specified engineered pNB esterase enzyme with a defined substrate of interest in the candidate solvent system, utilizing an enzyme activity assay, such as those described herein. The non-aqueous co-solvent component of an aqueous co-solvent system may be miscible with the aqueous component, providing a single liquid phase, or may be partly miscible or immiscible with the aqueous component, providing two liquid phases. Exemplary aqueous co-solvent systems can comprise water and one or more co-solvents selected from an organic solvent, polar solvent, and polyol solvent. In some embodiments, the co-solvent can be a polar solvent, such as DMF, DMSO, or lower alcohol.

In some embodiments of the process, the suitable reaction conditions comprise an aqueous co-solvent, where the co-solvent comprises DMF at about 1% to about 80% (v/v), about 1 to about 70% (v/v), about 2% to about 60% (v/v), about 5% to about 40% (Wvv), 10% to about 40% (v/v), 10% to about 30% (v/v), or about 10% to about 20% (v/v). In some embodiments of the process, the suitable reaction conditions comprise an aqueous co-solvent comprising DMF at least about 1%, 5%, 10%, 15%, 20%, 25%, 30%, 35%, 40%, 45%, 50%, 55%, 60%, 65%, 70%, 75%, or 80% (v/v). In some embodiments of the process, the suitable reaction conditions comprise an aqueous co-solvent comprising DMF of from about 5% (v/v) to about 45% (v/v), from about 10% (v/v) to about 30% (v/v), and in some embodiments a DMF concentration of about 15% (v/v).

The quantities of reactants used in the pNB esterase reaction will generally vary depending on the quantities of product desired, and concomitantly the amount of pNB esterase substrate employed. Those having ordinary skill in the art will readily understand how to vary these quantities to tailor them to the desired level of productivity and scale of production.

In some embodiments, the order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor, pNB esterase, and pNB esterase substrate may be added first to the solvent.

The solid reactants (e.g., enzyme, salts, substrate compounds, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a pre-chilled lyophilization chamber, followed by the application of a vacuum.

For improved mixing efficiency when an aqueous co-solvent system is used, the pNB esterase and cofactor may be added and mixed into the aqueous phase first. The organic phase may then be added and mixed in, followed by addition of the pNB esterase substrate. Alternatively, the pNB esterase substrate may be premixed in the organic phase, prior to addition to the aqueous phase.

The pNB esterase reaction is generally allowed to proceed until further conversion of pNB-protected substrate to product does not change significantly with reaction time, e.g., less than 10% of substrate being converted, or less than 5% of substrate being converted. In some embodiments, the reaction is allowed to proceed until there is complete or near complete conversion of pNB-protected substrate to the deprotected product compound. Transformation of substrate to product can be monitored using known methods by detecting substrate and/or product. Suitable methods include gas chromatography, HPLC, and the like. Conversion yields of the deprotected product compound generated in the reaction mixture are generally greater than about 509/o, may also be greater than about 60%, may also be greater than about 70%, may also be greater than about 80%, may also be greater than 90%, and may be greater than about 97%. In some embodiments, the methods for preparing the deprotected imipenem compound (1) using an engineered pNB esterase polypeptide under suitable reaction conditions results in at least about 91%, 92%, 93%, 94%, 95%, 96%, 97%, 98%, 99% or greater conversion of the pNB-protected substrate of compound (2), to the deprotected imipenem product of compound (1) in about 48 h or less, in about 36 h or less, in about 24 h or less, or even less time.

In some embodiments of the process, the suitable reaction conditions comprise a substrate loading of at least about 5 g/L, 10 g/L, 20 g/L, 30 g/L, 40 g/L, 50 g/L, 60 g/L, 70 g/L, 100 g/L, or more, and wherein the process results in at least about 70%, 75%, 80%, 85%, 90%, 91%, 92%, 93%, 94%, 95%, 96%, 97%, 98%, 99% or greater conversion of substrate compound to product compound in about 48 h or less, in about 36 h or less, or in about 24 h or less.

In a further embodiment of the processes, the suitable reaction conditions can comprise an initial substrate loading to the reaction solution which is then contacted by the engineered pNB esterase polypeptide. The reaction solution is then further supplemented with additional substrate compound as a continuous addition over time at a rate of at least about 1 g/L/h, at least about 2 g/L/h, at least about 4 g/L/h, at least about 6 g/L/h, or higher. Thus, according to these suitable reaction conditions, polypeptide is added to a solution having an initial substrate loading of at least about 5 g/L, 10 g/L, 20 g/L, 30 g/L, or 40 g/L. This addition of polypeptide is then followed by continuous addition of further substrate to the solution at a rate of about 2 g/L/h, 4 g/L/h, or 6 g/L/h until a much higher final substrate loading of at least about 30 g/L, 40 g/L, 50 g/L, 60 g/L, 70 g/L, 100 g/L, 150 g/L, 200 g/L or more, is reached. Accordingly, in some embodiments of the process, the suitable reaction conditions comprise addition of the polypeptide to a solution having an initial substrate loading of at least about 20 g/L, 30 g/L, or 40 g/L followed by addition of further substrate to the solution at a rate of about 2 g/L/h, 4 g/L/h., or 6 g/L/h until a final substrate loading of at least about 30 g/L, 40 g/L, 50 g/L, 60 g/L, 70 g/L, 100 g/L or more, is reached. This substrate supplementation reaction condition allows for higher substrate loadings to be achieved while maintaining high rates of conversion of the pNB-protected substrate to the deprotected product of at least about 91%, 92%, 93%, 94%, 95%, 96%, 97%, 98%, 99% or greater.

In some embodiments of the processes, the pNB esterase reaction can comprise the following suitable reaction conditions: (a) substrate loading at about 2 g/L to 200 g/L; (b) about 0.1 to 10 g/L of engineered pNB esterase polypeptide; (c) about 0.05 to 0.5 M MES buffer; (d) about 5% to about 20% (v/v) DMF co-solvent; (e) pH of about 6 to 8; and (f) temperature of about 10 to 35° C.

In some embodiments of the processes, the pNB esterase reaction can comprise the following suitable reaction conditions: (a) substrate loading at about 5 g/L to 100 g/L; (b) about 2 to 5 g/L of engineered pNB esterase polypeptide; (c) about 0.1 M MES buffer; (d) about 15% (v/v) DMF co-solvent; (e) pH of about 7; and (f) temperature of about 15° C.

In some embodiments, additional reaction components or additional techniques carried out to supplement the reaction conditions. These can include taking measures to stabilize or prevent inactivation of the pNB esterase polypeptide, reduce product compound inhibition, reduce undesirable side-product production, and/or shift reaction equilibrium to product compound formation.

In further embodiments, any of the above described processes for the conversion of substrate compound to product compound can further comprise one or more steps selected from: extraction, isolation, purification, and crystallization of product compound. Methods, techniques, and protocols for extracting, isolating, purifying, and/or crystallizing the product compound from the biocatalytic reaction mixtures produced by the above disclosed methods are known to the ordinary artisan and/or accessed through routine experimentation. Additionally, illustrative methods are provided in the Examples below.

Various features and embodiments of the disclosure are illustrated in the following representative examples, which are intended to be illustrative, and not limiting.

6. EXAMPLES

Example 1

Synthesis, Optimization, and Screening of Engineered pNB Esterase Polypeptides Gene Synthesis and Optimization: The polynucleotide sequence encoding the 489 amino acid wild-type pNB esterase polypeptide from *Bacillus subtilis* (Genbank Acc. No. AAA81915.1, GI: 468046) was codon optimized for expression in *E. coli* together with nucleotide changes encoding the following 7 amino acid substitutions: 160V, L144M, P317S, H322R, L334S, M358V, and Y370F. This codon-optimized gene, disclosed herein as SEQ ID NO: 1, was synthesized and cloned into a pCK 110900 vector system (see e.g., US Patent Application Publication 20060195947, which is hereby incorporated by reference herein) and subsequently expressed in *E. coli* W311fhuA. The *E. coli* W3110 expresses the pNB esterase polypeptides as an intracellular protein under the control of the lac promoter. The initial engineered polypeptide of SEQ ID NO: 2 did not have detectable activity in the conversion of the pNB-protected imipenem substrate compound (2) to imipenem of compound (1). Based on structural modeling of compound (2) of the active site of the wild-type pNB esterase, the engineered polypeptide of SEQ ID NO: 2 was further modified with the amino acid substitution M193A, resulting in the engineered pNB esterase polypeptide of SEQ ID NO: 4, which was found to have activity in the conversion of compound (2) to compound (1). The polynucleotide of SEQ ID NO: 3 (which encodes the engineered pNB esterase polypeptide of SEQ ID NO: 4) then was used as the starting backbone for further optimization using standard methods of directed evolution via iterative variant library generation by gene synthesis followed by screening and sequencing of the hits to generate genes encoding engineered pNB esterases capable of converting compound (2) to compound (1) with enhanced enzyme properties relative to the engineered polypeptide of SEQ ID NO: 4. The resulting engineered pNB esterase polypeptide sequences and specific mutations and relative activities are listed in Table 2 and the Sequence Listing.

Example 2

Production of Engineered pNB Esterases

The engineered pNB esterase polypeptides were produced in host *E. coli* W3110 as an intracellular protein expressed under the control of the lac promoter. The polypeptide accumulates primarily as a soluble cytosolic active enzyme. A shake-flask procedure is used to generate engineered polypeptide powders that can be used in activity assays or biocatalytic processes disclosed herein.

High-Throughput Growth and Expression. Cells are picked and grown overnight in LB media containing 1% glucose and 30 μg/mL chloramphenicol (CAM) under culture conditions of 30° C., 200 rpm, and 85% humidity. A 20 μL aliquot of overnight growth are transferred to a deep well plate containing 380 μL 2×YT growth media containing 30 μg/mL CAM, 1 mM IPTG, and incubated for ~18 h at 30° C. 200 rpm, and 85% humidity. Subculture TB media is made up of TB media (380 μL/well), 30 μg/mL CAM, and 1 mM IPTG. Cell cultures are centrifuged at 4000 rpm, 4° C. for 10 minutes, and the supernatant media discarded. Cell pellets are resuspended in 200 μL Lysis Buffer (0.1 M phosphate buffer, pH 7.5, containing 0.5 mg/mL PMBS and 1.0 mg/mL Lysozyme) and the lysate is used in the HTP assay as described below.

Production of Shake Flask Powders (SFP). A shake-flask procedure was used to generate engineered pNB esterase polypeptide powders used in secondary screening assays or in larger scale biocatalytic processes disclosed herein. Shake flask powder (SFP) includes approximately 30% total protein and accordingly provide a more purified preparation of an engineered enzyme as compared to the cell lysate used in HTP assays. A single colony of *E. coli* containing a plasmid encoding an engineered pNB esterase of interest is inoculated into 50 mL Luria Bertani broth containing 50 μg/ml chloramphenicol and 1% glucose. Cells are grown overnight (at least 16 hours) in an incubator at 30° C. with shaking at 250 rpm. The culture is diluted into 250 mL Terrific Broth (12 giL bacto-tryptone, 24 g/L yeast extract, 4 mL/L glycerol, 65 mM potassium phosphate, pH 7.0, 1 mM $MgSO_4$) containing 30 μg/ml chloramphenicol, in a 1 liter flask to an optical density of 600 nm ($OD_{600}$) of 0.2 and allowed to grow at 30° C. Expression of the pNB esterase gene is induced by addition of isopropyl-β-D-thiogalactoside ("IPTG") to a final concentration of 1 mM when the $OD_{600}$ of the culture is 0.6 to 0.8. Incubation is then continued overnight (at least 16 hours). Cells are harvested by centrifugation (5000 rpm, 15 min, 5° C.) and the supernatant discarded. The cell pellet is resuspended with 25 mL volume of cold (5° C.) 100 mM phosphate buffer, pH 7.0, and harvested by centrifugation as above. The washed cells are resuspended in 12 mL of the cold phosphate buffer and passed through a One Shot Cell Disrupter (Constant Systems Ltd.) at 40 kpsi and 5° C. Cell debris is removed by centrifugation (10000 rpm, 45 minutes, and 5° C.). The clear lysate supernatant is collected and stored at −20° C. Lyophilization of frozen clear lysate provides a dry shake-flask powder of crude pNB esterase polypeptide. Alternatively, the cell pellet (before or after washing) can be stored at 4° C. or −80° C.

Production of Downstream Process (DSP) Powders: DSP powders contain approximately 80% total protein and accordingly provide a more purified preparation of the engineered pNB esterase enzyme as compared to the cell lysate used in the high throughput assay. Larger-scale (~100-120 g) fermentation of the engineered pNB esterase polypeptides for production of DSP powders can be carried out as a short batch followed by a fed batch process according to standard bioprocess methods. Briefly, pNB esterase expression is induced by addition of IPTG to a final concentration of 1 mM. Following fermentation, the cells are harvested and resuspended in 100 mM phosphate buffer, pH 7, then mechanically disrupted by homogenization. The cell debris and nucleic acids are flocculated with polyethylenimine (PEI) and the suspension clarified by centrifugation. The resulting clear supernatant is concentrated using a tangential cross-flow ultrafiltration membrane to remove salts and water. The concentrated and partially purified enzyme concentrate can then be dried in a lyophilizer and packaged (e.g., in polyethylene containers).

Example 3

High Throughput (HTP) Screening of pNB Esterases for Conversion of pNB-Protected Substrate of Compound (2) to Compound (1), Imipenem HTP screening of cell lysates was used to guide primary selection of engineered pNB esterase polypeptides having improved properties for the conversion of substrate compound (2) to imipenem product compound (1).

For preparing the lysates, cells were grown in 96-well plates as described in Example 2 and lysates prepared by dispensing 200 μL Lysis Buffer (0.1 M phosphate buffer, pH 7.5, containing 0.5 mg/mL PMBS and 1.0 mg/mL Lysozyme) into each well. Plates were sealed, shaken for 2 h, and then centrifuged for 20 min at 4000 rpm, 4° C., to pellet the cell debris.

HTP Assay pNB Esterase Polypeptide Activity: A 45 μL aliquot of 0.1 M phosphate buffer at pH 7.5 and 125 μL of cell lysate was added to each well of a 96-well plate. Reactions were initiated by adding 30 μL aliquot of a stock substrate solution (13.5 μL of compound (2) dissolved in DMF) to each well. Plates were sealed, quickly spun in the centrifuge (<1 min), and placed in shaker at 200 rpm at 15° C. for 24 h. Reactions were quenched with 800 μL of acetonitrile and samples examined by HPLC as described in Example 4.

Example 4

Analytical Procedures

HPLC Analysis of Activity of HTP Reactions: Reactions were quenched by dispensing 800 μL of acetonitrile into each well (as in Example 3), heat sealing the plate, shaking at high speed for 1 min to mix, then spinning down the plate in a centrifuge at 4000 rpm, 10 min, at 4° C. A 200 μL aliquot of the quenched HTP reaction was dispensed into a 96 well round bottom plate for HPLC analysis. The 200 μL samples were subject to HPLC analysis under the following conditions.

| | | |
|---|---|---|
| Column | Poroshell EC C18, 2.6 μm, 4.6 × 100 mm with guard column | |
| Temperature | Not controlled | |
| Mobile Phase | Gradient: A: Acetonitrile/0.1% formic acid; B: Water/0.1% formic acid | |
| Time (min) | A % | B % |
| 0-1 | 2 | 98 |
| 2.8-4.0 | 72 | 28 |
| 4.2-5.0 | 2 | 98 |
| Flow Rate | 1.0 mL/min | |
| Detection | 315 nm, ref 400 nm | |
| Injection volume | 10 μL | |
| Retention Times | Compound (1), imipenem: 3.1-3.16 min<br>Compound (3) side-product (β-lactam ring opened imipenem): 3.6 min<br>Compound (2), pNB-protected imipenem: 3.8 min<br>p-nitrobenzyl alcohol: 4.1 min<br>Side product A (ring opened diacid of compound (2)): 1.2 min | |

Conversion of compound (2) to compound (1) was determined from the resulting chromatograms as follows:

Conversion (%)=Product Area/(Product Area+Substrate Area)×100%

Example 5

Process for Conversion of Compound (2) to Compound (1) at 1 mL Scale

SFP preparations of the engineered pNB esterase polypeptides were used in 1 mL scale reactions of the conversion of a pNB-protected imipenem substrate of compound (2) to the product imipenem of compound (1). These reactions demonstrate how these biocatalysts can be used for the preparation of carbapenem compounds such as imipenem. The reactions at 1 mL scale were carried out as follows. To a 2 mL glass vial was added 0.35 mL of 100 mM MES buffer (pH 7.0), 0.50 mL of a 2 g/L SFP preparation of pNB esterase polypeptide (SEQ ID NO: 76), and 0.15 mL of a 33.3 mg/mL solution of compound (2) in DMF. The mixture was placed in a Kuhner shaker at 200 rpm, for 2 h at 15° C. Final concentrations of components were: 5 g/L of compound (2); 15% v/v DMF: 5 g/L pNB esterase polypeptide SFP preparation; and 100 mM MES, at pH 7.0.

Samples of 20 μL were taken at different time points and diluted with 40 μL acetonitrile and shaken well. The sample was mixed with 340 μL of 100 mM MES buffer, mixed well and centrifuged for 10 min. The supernatant was analyzed by HPLC, using the instrument and parameters described in Example 4.

The HPLC time course profile results for the various pNB-esterases tested in 1 mL reactions are shown below in Table 3.

TABLE 3

| pNB esterase SEQ ID NO: | % Conversion to Compound (1) @ 1 h reaction time point | % Conversion to Compound (1) @ 2 h reaction time point |
|---|---|---|
| 54 | 20 | 32 |
| 76 | 63 | 73 |
| 80 | 60 | 73 |
| 116 | 75 | 81 |

The engineered pNB esterase polypeptide of SEQ ID NO: 116 reached 75% conversion of pNB-protected compound (2) to imipenem product compound (1) at 1 h, and 80% conversion after only 2 h. The polypeptides of SEQ ID NO: 76 and 80 performed with slightly lower compound (2) to compound (1) conversion rates under these same conditions.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An engineered polypeptide having p-nitrobenzyl esterase (pNB) activity, comprising an amino acid sequence having at least 90% identity to SEQ ID NO: 2 and one or more residue differences as compared to SEQ ID NO: 2 at residue positions selected from: 108, 115, 116, 130, 193, 214, 219, 273, 276 and 321, wherein the differences at positions 115 and 273 are 115Q/W and 273A/E/T/V, respectively, and optionally wherein said engineered polypeptide further comprises a different residue at position 362.

2. The engineered polypeptide of claim 1 in which the residue differences as compared to SEQ ID NO: 2 at the residue positions 108, 115, 116, 130, 193, 214, 219, 273, 276, 321, and 362 are selected from 108L/Y, 116S, 130T, 164T, 193A/D/E/V, 214G, 219A/D/L/V, 276A/T/L, 321A, and 362A/D/Q/S/V.

3. The engineered polypeptide of claim 1 in which the amino acid sequence comprises one or more residue differences as compared to SEQ ID NO: 2 selected from: 108L/Y, 193A/D/E/V, 219A/D/L/V, and 362A/D/Q/S/V.

4. The engineered polypeptide of claim 1 in which the amino acid sequence comprises a residue difference as compared to SEQ ID NO: 2 at position 193 selected from: 193A/D/E/V.

5. The engineered polypeptide of claim 4 in which the amino acid residue difference as compared to SEQ ID NO: 2 at position 193 is 193V.

6. The engineered polypeptide of claim 5 in which the amino acid sequence further comprises residue differences as compared to SEQ ID NO: 2 at positions 219 and 273 selected from 219L/V and 273A/V.

7. The engineered polypeptide of claim 6 in which the amino acid sequence further comprises residue differences as compared to SEQ ID NO: 2 at positions 108 and 362 selected from 108L/Y and 362A/D/Q/S/V.

8. The engineered polypeptide of claim 7 in which the amino acid sequence further comprises a residue difference as compared to SEQ ID NO: 2 at position 115 selected from 115Q/W.

9. The engineered polypeptide of claim 2 in which the amino acid sequence comprises a combination of residue differences as compared to SEQ ID NO: 2 selected from:

193V, 219V, and 273A;
108Y, 193D, 219V, 273A, and 362S;
108Y, 193V, 219V, 273A, and 362Q;
108Y, 115Q, 193V, 219L, 273A, and 362Q; and
108Y, 115Q, 193V, 219V, 273A, and 362Q.

10. The engineered polypeptide of claim 1 in which the amino acid sequence further comprises one or more residue differences as compared to SEQ ID NO: 2 selected from: 116S, 130T, 164T, 214G, 276A/T/L, and 321A.

11. The engineered polypeptide of claim 1 in which the amino acid sequence further comprises a residue difference as compared to SEQ ID NO: 2 selected from: 49G, 94G, 96S, 227T, 251V, 267R, 271L, 274L, 313F, 322C/Y, 343V, 356R, 359A, 398L, 412E, 437T, 464A, and 481R.

12. The engineered polypeptide of claim 1 in which the amino acid sequence does not comprise a residue difference as compared to SEQ ID NO: 2 at positions 60, 144, 317, 322, 334, 358, and 370.

13. The engineered polypeptide of claim 2 in which the pNB esterase has at least 1.2 fold, 2 fold, 5 fold, 10 fold, 20 fold, 25 fold, 50 fold, 75 fold, 100 fold, or greater increased activity as compared to the polypeptide of SEQ ID NO: 4 in converting compound (2) to compound (1) under suitable reaction conditions.

14. The engineered polypeptide of claim 1 in which the amino acid sequence comprises a sequence selected from SEQ ID NO: 4, 6, 8, 10, 12, 14, 16, 18, 20, 22, 24, 26, 28, 30, 32, 34, 36, 38,40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, and 120.

15. The engineered polypeptide of claim 1 in which the polypeptide is immobilized on a solid support.

16. The engineered polypeptide of claim 15 in which the solid support is a bead or resin comprising polymethacrylate with epoxide functional groups, polymethacrylate with amino epoxide functional groups, styrene/DVB copolymer or polymethacrylate with octadecyl functional groups.

17. A process for preparing compound (1), or a salt or hydrate of compound (1)

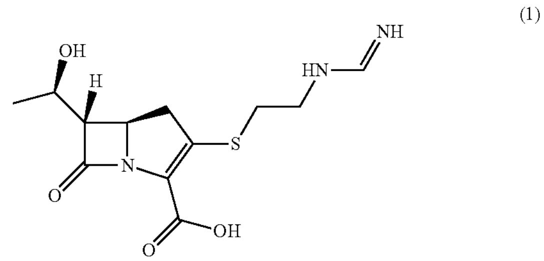 [SMILES: C[C@@H](O)[C@H]1C(=O)N2C(C(=O)O)=C(SCCNC=N)C[C@H]12]

wherein the method comprises contacting a substrate compound (2), or a salt or hydrate of compound (2)

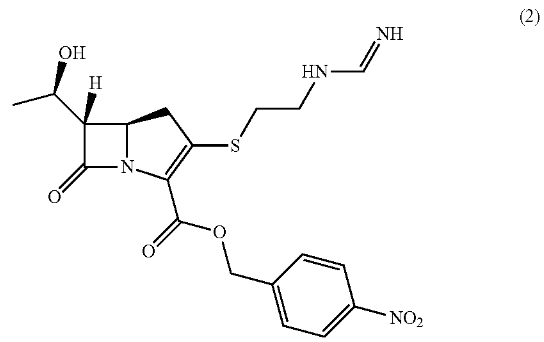 [SMILES: C[C@@H](O)[C@H]1C(=O)N2C(C(=O)OCc3ccc([N+](=O)[O-])cc3)=C(SCCNC=N)C[C@H]12]

with the engineered pNB esterase polypeptide of claim 1 under suitable reaction conditions.

18. The process of claim 17 in which the substrate of compound (2) is at a loading of from about 1 to about 200 g/L, from about 2 to about 100 g/L, or about 5 to about 50 g/L.

19. The process of claim 18 in which the substrate of compound (2) is at a loading of at least about 0.5 g/L, 1 g/L, 5 g/L, 10 g/L, 20 g/L, 30 g/L, 40 g/L, 50 g/L, 100 g/L, 150 g/L, or 200 g/L.

20. The process of claim 17 in which the suitable reaction conditions comprise a buffer selected from borate, phosphate, carbonate, triethanolamine (TEA), Tris, and 2-(N-morpholino)ethanesulfonic acid (MES).

21. The process of claim 20 in which the buffer comprises MES, wherein the MES concentration is about 0.01 to about 0.4 M, about 0.05 to about 0.4 M, about 0.1 to about 0.3 M, or about 0.1 to about 0.2 M.

22. The process of claim 21 in which the MES concentration is about 0.01 M, 0.02 M, 0.03 M, 0.04 M, 0.05 M, 0.07 M, 0.1 M, 0.12 M, 0.14 M, 0.16 M, 0.18 M, 0.2 M, 0.3 M, or 0.4 M.

23. The process of claim 17 in which the suitable reaction conditions comprise a pH from about 5 to about 10, pH from about 6 to about 9, or pH from about 7 to about 8.

24. The process of claim 23 in which the suitable reaction conditions comprise a pH of about 6, 6.5, 7, 7.5, 8, 8.5, 9, 9.5, or 10.

25. The process of claim 17 in which the suitable reaction conditions comprise a temperature of about 5° C. to about 65° C., about 10° C. to about 60° C., about 15° C. to about 55° C., about 15° C. to about 45° C., about 15° C. to about 35° C., about 20° C. to about 55° C., or about 30° C. to about 60° C.

26. The process of claim 25 in which the suitable reaction conditions comprise a temperature of about 5° C., 10° C., 15° C., 20° C., 25° C., 30° C., 35° C., 40° C., 45° C., 50° C., 55° C., 60° C., 65° C., or 70° C.

27. The process of claim 17 in which the suitable reaction conditions comprise dimethylformamide (DMF) as a co-solvent present at a concentration of from about 2% to about 30% v/v; or from about 5% to about 20% v/v.

28. The process of claim 27 in which the DMF is present at a concentration of about 2% v/v, 5% v/v, 10% v/v, 15% v/v, 20% v/v, 25% v/v, or 30% v/v.

29. The process of claim 17 in which the pNB esterase polypeptide is at a concentration of about 0.01 to about 50 g/L, about 0.05 to about 50 g/L, about 0.1 to about 40 g/L, about 1 to about 40 g/L, about 2 to about 40 g/L, about 5 to about 40 g/L, about 5 to about 30 g/L, about 0.1 to about 10 g/L, about 0.5 to about 10 g/L, about 1 to about 10 g/L, about 0.1 to about 5 g/L, about 0.5 to about 5 g/L, or about 0.1 to about 2 g/L.

30. The process of claim 29 in which the pNB esterase polypeptide is at a concentration of about 0.01 g/L, 0.05 g/L, 0.1 g/L, 0.2 g/L, 0.5 g/L, 1 g/L, 2 g/L, 5 g/L, 10 g/L, 15 g/L, 20 g/L, 25 g/L, 30 g/L, 35 g/L, 40 g/L, or 50 g/L.

31. The process of claim 17 in which the suitable reaction conditions comprise:

(a) substrate loading at about 2 g/L to 200 g/L;
(b) about 0.1 to 10 g/L of engineered pNB esterase polypeptide;
(c) about 0.05 to 0.5 M MES buffer;
(d) about 5% to about 20% (v/v) DMF co-solvent;
(e) pH of about 6 to 8; and
(f) temperature of about 10 to 35° C.

32. The process of claim 17 in which the suitable reaction conditions comprise:

(a) substrate loading at about 5 g/L to 100 g/L;
(b) about 2 to 5 g/L of engineered pNB esterase polypeptide;
(c) about 0.1 M MES buffer;
(d) about 15% (v/v) DMF co-solvent;
(e) pH of about 7; and
(f) temperature of about 15° C.

* * * * *